US008933019B2

(12) United States Patent
Debnath et al.

(10) Patent No.: US 8,933,019 B2
(45) **Date of Patent: *Jan. 13, 2015**

(54) ANTIVIRAL CELL-PENETRATING PEPTIDES

(71) Applicants: Asim Kumar Debnath, Fort Lee, NJ (US); Hongtao Zhang, Mt. Vernon, NY (US); Francesca Curreli, Bronx, NY (US)

(72) Inventors: Asim Kumar Debnath, Fort Lee, NJ (US); Hongtao Zhang, Mt. Vernon, NY (US); Francesca Curreli, Bronx, NY (US)

(73) Assignee: New York Blood Center, Inc., New York, NY (US)

( * ) Notice: Subject to any disclaimer, the term of this patent is extended or adjusted under 35 U.S.C. 154(b) by 74 days.

This patent is subject to a terminal disclaimer.

(21) Appl. No.: 13/664,699

(22) Filed: Oct. 31, 2012

(65) Prior Publication Data

US 2013/0059776 A1 Mar. 7, 2013

Related U.S. Application Data

(63) Continuation of application No. 12/436,080, filed on May 5, 2009, now Pat. No. 8,324,153.

(60) Provisional application No. 61/050,955, filed on May 6, 2008.

(51) Int. Cl.

*A61P 31/18* (2006.01)
*A61K 38/10* (2006.01)
*A61K 38/04* (2006.01)
*C07K 7/08* (2006.01)
*A61K 38/00* (2006.01)
*C07K 14/005* (2006.01)

(52) U.S. Cl.

CPC ..... *C07K 14/005* (2013.01); *C12N 2740/16222* (2013.01)

USPC ............................ 514/3.8; 514/21.5; 530/327

(58) Field of Classification Search

None

See application file for complete search history.

(56) References Cited

U.S. PATENT DOCUMENTS

| | | | | |
|---|---|---|---|---|
| 6,187,548 | B1 | 2/2001 | Akerstrom et al. | |
| 6,239,270 | B1 | 5/2001 | Akerstrom et al. | |
| 6,653,102 | B2 | 11/2003 | Roch et al. | |
| 6,790,950 | B2 | 9/2004 | Lowery et al. | |
| 7,723,469 | B2 | 5/2010 | Walensky et al. | |
| 7,763,262 | B2 | 7/2010 | Lowery et al. | |
| 7,820,786 | B2 | 10/2010 | Thomson | |
| 8,324,153 | B2 * | 12/2012 | Debnath et al. | 514/2.2 |
| 2005/0250680 | A1 | 11/2005 | Walensky et al. | |
| 2006/0008848 | A1 | 1/2006 | Verdine et al. | |
| 2009/0149630 | A1 | 6/2009 | Walensky et al. | |
| 2009/0176964 | A1 | 7/2009 | Walensky et al. | |
| 2010/0130430 | A1 | 5/2010 | Debnath | |
| 2010/0151483 | A1 | 6/2010 | Hornbeck et al. | |
| 2010/0159477 | A1 | 6/2010 | Hornbeck et al. | |
| 2010/0168288 | A1 | 7/2010 | Bernal et al. | |
| 2010/0267608 | A1 | 10/2010 | Das Gupta et al. | |
| 2010/0286057 | A1 | 11/2010 | Walensky et al. | |
| 2011/0218155 | A1 | 9/2011 | Walensky et al. | |
| 2011/0318352 | A1 | 12/2011 | Walensky et al. | |
| 2012/0165249 | A1 | 6/2012 | Debnath | |

FOREIGN PATENT DOCUMENTS

| | | | |
|---|---|---|---|
| WO | 98/40744 | A1 | 9/1998 |
| WO | 00/61724 | | 10/2000 |
| WO | 2005/044839 | A2 | 5/2005 |
| WO | 2008/045238 | A2 | 4/2008 |

OTHER PUBLICATIONS

Abdurahman, S. et al., "Selected ammo acid substitutions in the C-terminal region of human immunodeficiency virus type 1 capsid protein affect virus assembly and release", J Gen Virol 85, 2903-2913 (2004).

Bhattacharya Shibani et al., "Solution structure of a hydrocarbon stapled peptide inhibitor in complex with monomeric C-terminal domain of HIV-1 capsid", Journal of Biological Chemistry, vol. 283(24), Jun. 2008, pp. 16274-16278.

Chien, A.I. et al., "A domain directly C-terminal to the major homology region of human immunodeficiency type 1 capsid protein plays a crucial role in directing both virus assembly and incorporation of Gag-Pol", Virology 348, pp. 84-95 (2006).

Chu et al., "Mutations in the alpha-helix Directly C-terminal to the Major Homology Region of Human Immunodeficiency Virus Type 1 Capsid Protein Disrupt Gag Multimerization and Markedly Impair Virus Particle Production", J Biomed. Sci. 13, 645-56 (2006).

Derdeyn, C.A. et al., "Sensitivity of Human Immunodeficiency Virus Type 1 to the Fusion Inhibitor T-20 is Modulated by Coreceptor Specificity Defined by the V3 Loop of gp120", J Virol. 74(18), 8358-8367, (2000).

Derdowski, A. et al., "A Novel Pluorescence Resonance Energy Transfer Assay Demonstrates that the Human Immunodeficiency Virus Type 1 Pr55Gag I Domain Mediates Gag-Gag Interactions", The Journal of Virology 78, 1230-1242 (2004).

Dong, X. et al., "AP-3 directs the intracellular trafficking of HIV-I Gag and plays a key role in particle assembly", Cell 120, 663-674 (2005).

Douglas, CC. et al., "Investigation of N-terminal domain charged residues on the assembly and stability of HIV-I CA", Biochemistry 43, 10435-10441 (2004).

Forshey, B.M. et al., "C Formation of a human immunodeficiency virus type 1 core of optimal stability is crucial for viral replication", J Virol. 76, 5667-5677 (2002).

(Continued)

*Primary Examiner* — Maury Audet

(74) *Attorney, Agent, or Firm* — K&L Gates LLP; Louis C. Cullman; Michelle Glasky Bergman

(57) ABSTRACT

Disclosed herein are cell penetrating peptides useful as treatment for Human Immunodeficiency Virus.

7 Claims, 8 Drawing Sheets

(56) References Cited

OTHER PUBLICATIONS

Freed, E.O., "HIV-I gag proteins: diverse functions in the virus life cycle", Virology 251, 1-15 (1998).

Gottlinger, H.G, "The HIV-I assembly machine", AIDS Suppl 5, S13-S20 (2001).

Grigorov, B. et al., "Assembly of infectious HPV-I in human epithelial and T-lymphoblastic cell lines", J Mol Biol. 359, 848-862 (2006).

Gross, I. et al., "N-terminal Extension of Human Immunodeficiency Virus Capsid Protein Converts the In Vitro Assembly Phenotype from Tubular to Spherical Particles", J. Virol 72 (16), 4798-4810, (1998).

Guo, X. et al., "The R362A mutation at the C-terminus of CA inhibits packaging of human immunodeficiency virus type 1 RNA", Virology 343, 190-200 (2005).

Joshi, A. et al., "Mutation of dileucine-like motifs in the human immunodeficiency virus type 1 capsid disrupts virus assembly, gag-gag interactions, gag-membrane binding, and virion maturation", J Virol. 80, 7939-7951 (2006).

Kieber-Emmons et al., Therapeutic peptdies and peptidomimetics, Protein Engineering, 435-441 (1997).

Kramer, B. et al., "HIV interaction with endosomes in macrophages and dendritic cells", Blood Cells Mol Dis. 35, 136-142 (2005).

Leduc, A.M. et al., "Helix-stabilized cyclic peptides as selective inhibitors of steroid receptor-coactivator interactions", Proc Natl Acad Sci U.S.A. 100 (20), 11273-11278 (2003).

Lundberg, M. et al., "Positively charged DNA-Binding Proteins Cause Apparent Cell Membrane Translocation", Biochem. Biophys. Res. Commun., 291, 367-371, (2002).

Morikawa, Y. "HIV capsid assembly", Curr HIV Res I, 1-14 (2003).

Nydegger S., et al., "HIV-I egress is gated through late endosomal membranes", Traffic. 4, 902-910 (2003).

Ono, A. & Freed, E.O. "Cell-type-dependent targeting of human immunodeficiency virus type 1 assembly to the plasma membrane and the multivesicular body", J Virol. 78(3), 1552-1563 (2004).

Pelchen-Matthews, A., et al., "Infectious HIV-I assembles in late endosomes in primary macrophages", J. Cell Biol. 162(3), 443-455 (2003).

Phelan et al., "A General Method for Constraining Short Peptides to an a-Helical Conformation", J. Am. Chem. Soc. 119(3), 455-460 (1997).

Qiu, W. et al., "Convenient, Large-Scale Asymmetric Synthesis of Enantiomerically pure trans-cinnamylglycine and - alpha-Alaine", Tetrahedron, 56, 2577-2582, (2000).

Richard, JP et al., "Cell penetrating peptides", J. Biol. Chem., 278(1), 585-590 (2003).

Ripka et al., "Peptidomimetic Design". Curr. Opin. Chem. Biol. 2, 441-452 (1998).

Sanderson. "Small Noncovalent Serine Protease Inhibitors", Med. Res. Rev. 19, 179-197 (1999).

Sherer, N.M. et al., "Visualization of retroviral replication in living cells reveals budding into multivesicular bodies", Traffic 4, 785-801 (2003).

Shoelson et al., "YMXM motifs of IRS-1 define substrate specificity of the insulin receptor kinase", PNAS (1992), 89(6), 2027-31).

Wang, D.et al., "Enhanced Metabolic Stability and Protein-Binding Properties of Artificial Helices Derived from a Hydrogen-Bond Surrogate: Application to Bcl-xL", Angewandte Chemie International Edition 44 (40), 6525-6529 (2005).

Yang et al., "Synthesis and helical structure of lactam bridged BH3 peptides derived from pro-apoptotic Bcl-2 family proteins", Bioorganic & Medicinal Chemistry Letters 14, 1403-1406 (2004).

Debnath et al. "Structure-Based Identification of Small Molecule Antiviral Compounds Targeted to the gp41 Core Structure of the Human Immunodeficiency Virus Type 1." J. Med. Chem. 1999, 42, 3203-3209.

Del Alamo et al. "Thermodynamic Dissection of a Low Affinity Protein—Protein Interface Involved in Human Immunodeficiency Virus Assembly." The Journal of Biological Chemistry, vol. 278, No. 30, pp. 27923-27929, 2003.

Ehrlich et al. "HIV-1 Capsid Protein Forms Spherical (Immature-Like) and Tubular (Mature-Like) Particles in Vitro: Structure Switching by pH-induced Conformational Changes." Biophysical Journal, vol. 81, 586-594, 2001.

Ganser-Pornillos et al. "Assembly Properties of the Human Immunodeficiency Virus Type 1 CA Protein." Journal of Virology, 2004, p. 2545-2552, vol. 78, No. 5.

Garzon et al. "The dimerization domain of the HIV-1 capsid protein binds a capsid protein-derived peptide: A biophysical characterization." Protein Science, 2004, 13:1512-1523.

Gross et al. "In vitro assembly propertied of purified bacterially expressed capsid proteins of human immunodeficiency virus." Eur. J. Biochem. 249, 592-600, 1997.

Hoglund et al. "Tripeptide Interference with Human Immunodeficiency Virus Type 1 Morphogenesis." Antimicrobial Agents and Chemotherapy, 2002, p. 3597-3605, vol. 46, No. 11.

Huseby et al. "Assembly of Human Immunodeficiency Virus Precursor Gag Proteins." The Journal of Biological Chemistry, vol. 280, No. 18, p. 17664-17670, 2005.

Jiang et al. "Enhancement of Human Immunodeficiency Virus Type 1 Infection by Antisera to Peptides from the Envelope Glycoproteins gp120/gp41." J. Exp. Med. vol. 174, 1991, 1557-1563.

Jiang et al. "A screening assay for antiviral compounds targeted to the HIV-1 gp41 core structure using a conformation-specific monoclonal antibody." Journal of Virological Methods 80, 1999, 85-96.

Jiang et al. "Development of HIV Entry Inhibitors Targeted to the Coiled-Coil Regions of gp41." Biochemical and Biophysical Research Communications 269, 641-646, 2000.

Jiang et al. "N-Substituted Pyrrole Derivative as Novel Human Immunodeficiency Virus Type 1 Entry Inhibitors that Interfere with the gp41 Six-Helix Bundle Formation and Block Virus Fusion." Antimicrobial Agents and Chemotherapy, 2004, p. 4349-4359, vol. 48, No. 11.

Lalezari et al. "Enfuvirtide, an HIV-1 Fusion Inhibitor, for Drug-Resistant HIV Infection in North and South America." The New England Journal of Medicine, 2003, vol. 348, No. 22.

Li et al. "PA-457: A potent HIV inhibitor that disrupts core condensation by targeting a late step in Gag processing." PNAS, 2003, vol. 100, No. 23, 13555-13560.

Liu et al. "Theaflavin derivatives in black tea and catechin derivatives in green tea inhibit HIV-1 entry by targeting gp41." Biochimica et Biophysica Acta 1723, 2005, 270-281.

Naicker et al. "Synthesis and anti-HIV-1 activity of 4-[4-(4,6-bisphenylamino-[1,3,5]triazin-2-ylamino)-5-methoxy-2-methylphenylazo]-5-hydroxynaphthalene-2,7-disulfonic acid and its derivatives." Bioorganic & Medicinal Chemistry 12, 2004, 1215-1220.

Neurath et al. "Blocking of CD4 Cell Receptors for the Human Immunodeficiency Virus Type 1 (HIV-1) by Chemically Modified Bovine Milk Proteins: Potential for AIDS Prophylaxis." Journal of Molecular Recognition, vol. 8, 304-316, 1995.

Neurath et al. "Structural Requirements for and Consequences of an Antiviral Porphyrin Binding to the V3 Loop of the Human Immunodeficiency Virus (HIV-1) Envelope of Glycoprotein gp120." Journal of Molecular Recognition, vol. 8, 345-357, 1995.

Neurath et al. "Cellulose acetate phthalate, a common pharmaceutical excipient, inactivates HIV-1 and blocks the coreceptor binding site on the virus envelope glycoprotein gp120." BMC Infectious Diseases 2001, 1:17.

Neurath et al. "Anti-HIV-1 activity of cellulose acetate phthalate: Synergy with soluble CD4 and induction of "dead end" gp41 six helix bundles." BMC Infectious Diseases 2002, 2:6.

Niedrig et al. "Inhibition of infectious human immunodeficiency virus type 1 particle formation by Gag protein-derived peptides." Journal of General Virology, 1994, 75, 1469-1474.

Sakalian et al. "3-O-(3',3'-Dimethysuccinyl) Betulinic Acid Inhibits Maturation of the Human Immunodeficiency Virus Type 1 Gag Precursor Assembled in Vitro." Journal of Virology, 2006, p. 5716-5722, vol. 80, No. 12.

Schafmeister et al. "An All-Hydrocarbon Cross-Linking System for Enhancing the Helicity and Metabolic Stability of Peptides." J. Am. Chem. Soc. 2000, 122, 5891-5892.

(56) References Cited

OTHER PUBLICATIONS

Sticht et al. "A peptide inhibitor of HIV-1 assembly in vitro." Nature Structural & Molecular Biology, vol. 12, No. 8, 2005.

Tang et al. "Antiviral Inhibition of the HIV-1 Capsid Protein." J. Mol. Biol., 2003, 327, 1013-1020.

Ternois et al. "The HIV-1 capsid protein C-terminal domain in complex with a virus assembly inhibitor." Nature Structural & Molecular Biology, vol. 12, No. 8, 2005.

Walensky et al. "Activation of Apoptosis in Vivo by a Hydrocarbon-Stapled BH3 Helix." Science, 2004, 3005(5689): 1466-1470.

Zhang et al. "A Cell-penetrating Helical Peptide as a Potential HIV-1 Inhibitor." J. Mol. Biol. 2008; 378(3) 565-580.

Zhao et al. "XTT Formazan Widely Used to Detect Cell Viability Inhibits HIV Type 1 Infection in Vitro by Targeting gp41." AIDS Research and Human Retroviruses, vol. 18, No. 14, 2002, pp. 989-997.

Zhao et al. "A novel assay to identify entry inhibitors that block binding of HIV-1 gp120 to CCR5." Virology 326, 2004, 299-309.

* cited by examiner

| | | Sequence ID No: |
|---|---|---|
| HIV-1 Dimer Interface | E-Q-A-S-Q-E-V-K-N-W-M-T-E-T-L-L-V-Q-N-A-N | 2 |
| NYAD-201 |  A-Q-E-V-K-X-W-M-T-X-T-L-L-V-A | 4 |
| NYAD-202 |  A-Q-A-V-K-X-W-M-T-X-T-L-L-V-A | 5 |
| NYAD-203 |  A-Q-E-V-K-X-W-M-T-X-T-L-L-V-A-K-K-K | 6 |
| NYAD-209 | A-Q-E-V-K-N-W-M-T-E-T-L-L-V-A | 3 |
| NYAD-210 |  A-Q-K-V-E-X-W-M-T-X-T-L-L-V-A | 7 |
| NYAD-212 |  A-Q-A-V-K-X-W-M-T-X-T-L-L-V-E-N-A | 8 |
| NYAD-214 |  A-Q-A-V-K-X-W-M-T-X-T-L-L-K-A-N-A-E | 9 |
| NYAD-215 (Scrambled) |  E-Q-L-V-W-X-K-M-T-X-A-L-A-V-T | 10 |
| NYAD-216 | FITC-ß-Ala-A-Q-E-V-K-N-W-M-T-E-T-L-L-V-A | 11 |

NYAD-218 A-Q-A-V-K-N-W-M-T-X-T-L-L-X-A 12
NYAD-219 A-Q-A-W-K-X-W-A-T-X-T-L-L-V-A-E 13
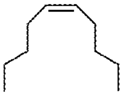
NYAD-220 A-Q-A-V-K-X-W-M-E-X-T-L-K-V-A-E 14
NYAD-221 A-Q-A-V-K-Z-W-M-T-E-T-L-X-V-A 15
NYAD-222 A-Q-A-W-K-Z-W-A-T-E-T-L-X-V-A-N 16
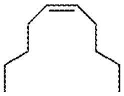
NYAD-223 I-A-Q-A-K-V-E-X-W-M-T-X-T-L-L-V-A-N 17
*FIG. 1-2*

FIG. 4
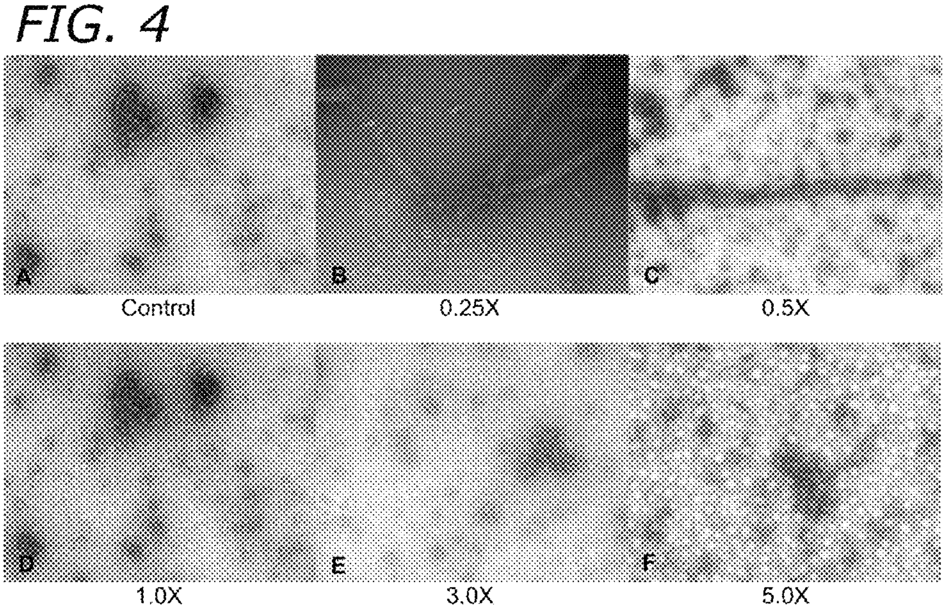
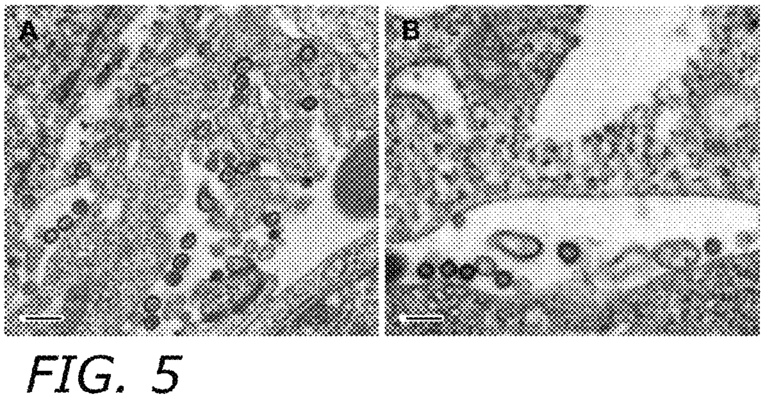
FIG. 5

SEQUENCE LISTING

```
<160> NUMBER OF SEQ ID NOS: 19

<210> SEQ ID NO 1
<211> LENGTH: 231
<212> TYPE: PRT
<213> ORGANISM: Human immunodeficiency virus type 1

<400> SEQUENCE: 1

Pro Ile Val Gln Asn Leu Gln Gly Gln Met Val His Gln Ala Ile Ser
1               5                   10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Glu Thr Ile Asn Glu Glu Ala Ala Glu Trp
65                  70                  75                  80

Asp Arg Leu His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr His Asn Pro Pro Ile Pro Val Gly Glu
        115                 120                 125

Ile Tyr Lys Arg Trp Ile Ile Leu Gly Leu Asn Lys Ile Val Arg Met
    130                 135                 140

Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Gly
        195                 200                 205

Ala Thr Leu Glu Glu Met Met Thr Ala Cys Gln Gly Val Gly Gly Pro
    210                 215                 220

Gly His Lys Ala Arg Val Leu
225                 230


<210> SEQ ID NO 2
<211> LENGTH: 21
<212> TYPE: PRT
<213> ORGANISM: Human immunodeficiency virus type 1
```

<400> SEQUENCE: 2

Glu Ala Gln Ser Gln Glu Val Lys Asn Trp Met Thr Glu Thr Leu Leu
1 5 10 15

Val Gln Asn Ala Asn
20

<210> SEQ ID NO 3
<211> LENGTH: 15
<212> TYPE: PRT
<213> ORGANISM: Artificial
<220> FEATURE:
<223> OTHER INFORMATION: Stapled peptide NYAD-209

<400> SEQUENCE: 3

Ala Gln Glu Val Lys Asn Trp Met Thr Glu Thr Leu Leu Val Ala
1 5 10 15

<210> SEQ ID NO 4
<211> LENGTH: 15
<212> TYPE: PRT
<213> ORGANISM: Artificial
<220> FEATURE:
<223> OTHER INFORMATION: Stapled peptide NYAD-201
<220> FEATURE:
<221> NAME/KEY: MISC_FEATURE
<222> LOCATION: (6)..(6)
<223> OTHER INFORMATION: X=(S)-a-2-(4'-pentenyl)alanine
<220> FEATURE:
<221> NAME/KEY: MISC_FEATURE
<222> LOCATION: (10)..(10)
<223> OTHER INFORMATION: X=(S)-a-2-(4'-pentenyl)alanine

<400> SEQUENCE: 4

Ala Gln Glu Val Lys Xaa Trp Met Thr Xaa Thr Leu Leu Val Ala
1 5 10 15

<210> SEQ ID NO 5
<211> LENGTH: 15
<212> TYPE: PRT
<213> ORGANISM: Artificial
<220> FEATURE:
<223> OTHER INFORMATION: Stapled peptide NYAD-202
<220> FEATURE:
<221> NAME/KEY: MISC_FEATURE
<222> LOCATION: (6)..(6)
<223> OTHER INFORMATION: X=(S)-a-2-(4'-pentenyl)alanine
<220> FEATURE:
<221> NAME/KEY: MISC_FEATURE
<222> LOCATION: (10)..(10)
<223> OTHER INFORMATION: X=(S)-a-2-(4'-pentenyl)alanine

<400> SEQUENCE: 5

Ala Gln Ala Val Lys Xaa Trp Met Thr Xaa Thr Leu Leu Val Ala
1 5 10 15

<210> SEQ ID NO 6
<211> LENGTH: 18
<212> TYPE: PRT
<213> ORGANISM: Artificial
<220> FEATURE:
<223> OTHER INFORMATION: Stapled peptide NYAD-203
<220> FEATURE:
<221> NAME/KEY: MISC_FEATURE
<222> LOCATION: (6)..(6)
<223> OTHER INFORMATION: X=(S)-a-2-(4'-pentenyl)alanine
<220> FEATURE:
<221> NAME/KEY: MISC_FEATURE
<222> LOCATION: (10)..(10)
<223> OTHER INFORMATION: X=(S)-a-2-(4'-pentenyl)alanine

<400> SEQUENCE: 6

Ala Gln Glu Val Lys Xaa Trp Met Thr Xaa Thr Leu Leu Val Ala Lys
1 5 10 15

Lys Lys

<210> SEQ ID NO 7
<211> LENGTH: 15
<212> TYPE: PRT
<213> ORGANISM: Artificial
<220> FEATURE:
<223> OTHER INFORMATION: Stapled peptide NYAD-210
<220> FEATURE:
<221> NAME/KEY: MISC_FEATURE
<222> LOCATION: (6)..(6)
<223> OTHER INFORMATION: X=(S)-a-2-(4'-pentenyl)alanine
<220> FEATURE:
<221> NAME/KEY: MISC_FEATURE
<222> LOCATION: (10)..(10)
<223> OTHER INFORMATION: X=(S)-a-2-(4'-pentenyl)alanine

<400> SEQUENCE: 7

Ala Gln Lys Val Glu Xaa Trp Met Thr Xaa Thr Leu Leu Val Ala
1 5 10 15

<210> SEQ ID NO 8
<211> LENGTH: 17
<212> TYPE: PRT
<213> ORGANISM: Artificial
<220> FEATURE:
<223> OTHER INFORMATION: Stapled peptide NYAD-212
<220> FEATURE:
<221> NAME/KEY: MISC_FEATURE
<222> LOCATION: (6)..(6)
<223> OTHER INFORMATION: X=(S)-a-2-(4'-pentenyl)alanine
<220> FEATURE:
<221> NAME/KEY: MISC_FEATURE
<222> LOCATION: (10)..(10)
<223> OTHER INFORMATION: X=(S)-a-2-(4'-pentenyl)alanine

<400> SEQUENCE: 8

Ala Gln Ala Val Lys Xaa Trp Met Thr Xaa Thr Leu Leu Val Glu Asn
1 5 10 15

Ala

<210> SEQ ID NO 9
<211> LENGTH: 18
<212> TYPE: PRT
<213> ORGANISM: Artificial
<220> FEATURE:
<223> OTHER INFORMATION: Stapled peptide NYAD-214
<220> FEATURE:
<221> NAME/KEY: MISC_FEATURE
<222> LOCATION: (6)..(6)
<223> OTHER INFORMATION: X=(S)-a-2-(4'-pentenyl)alanine
<220> FEATURE:
<221> NAME/KEY: MISC_FEATURE
<222> LOCATION: (10)..(10)
<223> OTHER INFORMATION: X=(S)-a-2-(4'-pentenyl)alanine

<400> SEQUENCE: 9

Ala Gln Ala Val Lys Xaa Trp Met Thr Xaa Thr Leu Leu Lys Ala Asn
1 5 10 15

Ala Glu

<210> SEQ ID NO 10
<211> LENGTH: 15
<212> TYPE: PRT

<213> ORGANISM: Artificial
<220> FEATURE:
<223> OTHER INFORMATION: Stapled peptide NYAD-215
<220> FEATURE:
<221> NAME/KEY: MISC_FEATURE
<222> LOCATION: (6)..(6)
<223> OTHER INFORMATION: X=(S)-a-2-(4'-pentenyl)alanine
<220> FEATURE:
<221> NAME/KEY: MISC_FEATURE
<222> LOCATION: (10)..(10)
<223> OTHER INFORMATION: X=(S)-a-2-(4'-pentenyl)alanine

<400> SEQUENCE: 10

```
Glu Gln Leu Val Trp Xaa Lys Met Thr Xaa Ala Leu Ala Val Thr
1               5                   10                  15
```

<210> SEQ ID NO 11
<211> LENGTH: 15
<212> TYPE: PRT
<213> ORGANISM: Artificial
<220> FEATURE:
<223> OTHER INFORMATION: Fluorescence-labeled peptide
<220> FEATURE:
<221> NAME/KEY: MOD_RES
<222> LOCATION: (1)..(1)
<223> OTHER INFORMATION: FITC derivatization

<400> SEQUENCE: 11

```
Ala Gln Glu Val Lys Asn Trp Met Thr Glu Thr Leu Leu Val Ala
1               5                   10                  15
```

<210> SEQ ID NO 12
<211> LENGTH: 15
<212> TYPE: PRT
<213> ORGANISM: Artificial
<220> FEATURE:
<223> OTHER INFORMATION: Stapled peptide  NYAD-218
<220> FEATURE:
<221> NAME/KEY: MISC_FEATURE
<222> LOCATION: (10)..(10)
<223> OTHER INFORMATION: X=(S)-a-2-(4'-pentenyl)alanine
<220> FEATURE:
<221> NAME/KEY: MISC_FEATURE
<222> LOCATION: (14)..(14)
<223> OTHER INFORMATION: X=(S)-a-2-(4'-pentenyl)alanine

<400> SEQUENCE: 12

```
Ala Gln Ala Val Lys Asn Trp Met Thr Xaa Thr Leu Leu Xaa Ala
1               5                   10                  15
```

<210> SEQ ID NO 13
<211> LENGTH: 16
<212> TYPE: PRT
<213> ORGANISM: Artificial
<220> FEATURE:
<223> OTHER INFORMATION: Stapled peptide NYAD-219
<220> FEATURE:
<221> NAME/KEY: MISC_FEATURE
<222> LOCATION: (6)..(6)
<223> OTHER INFORMATION: X=(S)-a-2-(4'-pentenyl)alanine
<220> FEATURE:
<221> NAME/KEY: MISC_FEATURE
<222> LOCATION: (10)..(10)
<223> OTHER INFORMATION: X=(S)-a-2-(4'-pentenyl)alanine

<400> SEQUENCE: 13

```
Ala Gln Ala Trp Lys Xaa Trp Ala Thr Xaa Thr Leu Leu Val Ala Glu
1               5                   10                  15
```

<210> SEQ ID NO 14
<211> LENGTH: 16

<212> TYPE: PRT
<213> ORGANISM: Artificial
<220> FEATURE:
<223> OTHER INFORMATION: Stapled peptide NYAD-220
<220> FEATURE:
<221> NAME/KEY: MISC_FEATURE
<222> LOCATION: (6)..(6)
<223> OTHER INFORMATION: X=(S)-a-2-(4'-pentenyl)alanine
<220> FEATURE:
<221> NAME/KEY: MISC_FEATURE
<222> LOCATION: (10)..(10)
<223> OTHER INFORMATION: X=(S)-a-2-(4'-pentenyl)alanine

<400> SEQUENCE: 14

Ala Gln Ala Val Lys Xaa Trp Met Glu Xaa Thr Leu Lys Val Ala Glu
1               5                   10                  15

<210> SEQ ID NO 15
<211> LENGTH: 15
<212> TYPE: PRT
<213> ORGANISM: Artificial
<220> FEATURE:
<223> OTHER INFORMATION: Stapled peptide NYAD-221
<220> FEATURE:
<221> NAME/KEY: MISC_FEATURE
<222> LOCATION: (6)..(6)
<223> OTHER INFORMATION: X=(R)-a-2-(7'-octenyl)alanine
<220> FEATURE:
<221> NAME/KEY: MISC_FEATURE
<222> LOCATION: (13)..(13)
<223> OTHER INFORMATION: X=(S)-a-2-(4'-pentenyl)alanine

<400> SEQUENCE: 15

Ala Gln Ala Val Lys Xaa Trp Met Thr Glu Thr Leu Xaa Val Ala
1               5                   10                  15

<210> SEQ ID NO 16
<211> LENGTH: 16
<212> TYPE: PRT
<213> ORGANISM: Artificial
<220> FEATURE:
<223> OTHER INFORMATION: Stapled peptide NYAD-222
<220> FEATURE:
<221> NAME/KEY: MISC_FEATURE
<222> LOCATION: (6)..(6)
<223> OTHER INFORMATION: X=(R)-a-2-(7'-octenyl)alanine
<220> FEATURE:
<221> NAME/KEY: MISC_FEATURE
<222> LOCATION: (13)..(13)
<223> OTHER INFORMATION: X=(S)-a-2-(4'-pentenyl)alanine

<400> SEQUENCE: 16

Ala Gln Ala Trp Lys Xaa Trp Ala Thr Glu Thr Leu Xaa Val Ala Asn
1               5                   10                  15

<210> SEQ ID NO 17
<211> LENGTH: 18
<212> TYPE: PRT
<213> ORGANISM: Artificial
<220> FEATURE:
<223> OTHER INFORMATION: Stapled peptide NYAD-223
<220> FEATURE:
<221> NAME/KEY: MISC_FEATURE
<222> LOCATION: (8)..(8)
<223> OTHER INFORMATION: X=(S)-a-2-(4'-pentenyl)alanine
<220> FEATURE:
<221> NAME/KEY: MISC_FEATURE
<222> LOCATION: (12)..(12)
<223> OTHER INFORMATION: X=(S)-a-2-(4'-pentenyl)alanine

<400> SEQUENCE: 17

Ile Ala Gln Ala Lys Val Glu Xaa Trp Met Thr Xaa Thr Leu Leu Val

-continued 1 5 10 15

Ala Asn

<210> SEQ ID NO 18
<211> LENGTH: 14
<212> TYPE: PRT
<213> ORGANISM: Artificial
<220> FEATURE:
<223> OTHER INFORMATION: antiviral peptide
<220> FEATURE:
<221> NAME/KEY: VARIANT
<222> LOCATION: (1)..(1)
<223> OTHER INFORMATION: X=Q or A
<220> FEATURE:
<221> NAME/KEY: VARIANT
<222> LOCATION: (2)..(2)
<223> OTHER INFORMATION: X=E, A or K
<220> FEATURE:
<221> NAME/KEY: VARIANT
<222> LOCATION: (3)..(3)
<223> OTHER INFORMATION: X=V or W
<220> FEATURE:
<221> NAME/KEY: VARIANT
<222> LOCATION: (4)..(4)
<223> OTHER INFORMATION: X=E or K
<220> FEATURE:
<221> NAME/KEY: VARIANT
<222> LOCATION: (7)..(7)
<223> OTHER INFORMATION: X=M or A
<220> FEATURE:
<221> NAME/KEY: VARIANT
<222> LOCATION: (13)..(13)
<223> OTHER INFORMATION: X=V or K
<220> FEATURE:
<221> NAME/KEY: VARIANT
<222> LOCATION: (14)..(14)
<223> OTHER INFORMATION: X=Q, A or E

<400> SEQUENCE: 18

Xaa Xaa Xaa Xaa Asn Trp Xaa Thr Glu Thr Leu Leu Xaa Xaa
1 5 10

<210> SEQ ID NO 19
<211> LENGTH: 15
<212> TYPE: PRT
<213> ORGANISM: Artificial
<220> FEATURE:
<223> OTHER INFORMATION: antiviral peptide

<400> SEQUENCE: 19

Ala Gln Ala Val Lys Asn Trp Met Thr Glu Thr Leu Leu Val Ala
1 5 10 15

ANTIVIRAL CELL-PENETRATING PEPTIDES

CROSS-REFERENCE TO RELATED APPLICATIONS

This application is a continuation of U.S. patent application Ser. No. 12/436,080 filed May 5, 2005 which claims the benefit under 37 CFR §119(e) to U.S. Provisional Patent Application 61/050,955 filed May 6, 2008, both of which are incorporated by reference herein in their entirety.

FIELD OF THE INVENTION

Disclosed herein are cell penetrating peptides useful as therapeutics for Human Immunodeficiency Virus.

BACKGROUND OF THE INVENTION

Human immunodeficiency virus type 1 (HIV-1) is the etiological agent that causes acquired immunodeficiency syndrome (AIDS). According to the AIDS Epidemic Update (*UNAIDS, December* 2007) approximately 36 million people are living with human immunodeficiency virus type-1 (HIV-1). Although the most severely affected areas are in Sub-Saharan Africa and South-East Asia, more than 2 million people are living with this disease in North America, Western and Central Europe. A significant increase in HIV infection in African Americans has been reported and HIV/AIDS was the leading cause of death among the African American women in 2002 in the US. Therefore, the AIDS epidemic is still a major health concern worldwide. The clinically useful anti-HIV drugs are primarily targeted to the reverse transcriptase (RT) and protease (PR), two vital enzymes in HIV-1 life cycle; however, a new drug targeted to another essential enzyme, integrase, has been recently approved by the United States Food and Drug Administration. The introduction of highly active anti-retroviral therapy (HAART) has significantly contributed to the decreased morbidity and mortality among HIV-1 infected individuals. However, the development of resistance to those drugs often poses a serious threat to the treatment options available to patients.

After an intense effort for more than 10 years a peptide-based drug targeted to the HIV-1 entry, T-20 (enfuvirtide), was developed and approved by the FDA in early 2003. The drug, although expensive, showed its potential in treating patients who are non-respondent to the other available drugs. This success is the testament to the fact that it is important to identify critical steps in HIV-1 life cycle and use them as new targets for possible intervention of HIV-1 infection. Recent reports of failure of HIV vaccine trials and microbicide trials validated the critical need to identify and utilize newer targets to develop new classes of anti-HIV-1 therapies.

The HIV-1 genome is composed of three major genes, gag, pol and env. The gag gene encodes the Gag polyprotein, the critical structural protein of HIV-1, whereas pol encodes viral enzymes, such as reverse transcriptase (RT), protease (PR) and integrase (IN), essential for HIV life cycle and env encodes the viral envelope proteins (Env). Assembly, a critical step in the HIV-1 life cycle, is generally thought to occur through the controlled polymerization of the Gag polyprotein, which is transported to the plasma membrane, where assembly takes place. Virus particles are then formed and bud out as spherical immature non-infectious particles. Immediately after budding, the particles undergo a process known as maturation. During this step, the Gag protein is sequentially cleaved by viral protease to matrix (MA), capsid (CA), nucleocapsid (NC), and p6 domains, as well as two spacer proteins, SP1 and SP2. This process triggers a dramatic change in the morphology of the particles, and an electrodense core is formed surrounded by the conical capsid. The formation of the mature capsid plays a critical role in viral infectivity. Gag has been shown to be essential and sufficient to form virus-like particles (VLP) in the absence of any other proteins or viral RNA. This led to many subsequent studies in determining the regions of gag responsible for HIV-1 assembly by genetic approaches. Data obtained through deletion, insertion and substitution of amino acids in Gag have identified three regions of Gag most important for viral assembly. They have been termed as the membrane binding domain or M-domain, the interacting domain or I-domain and the late domain of L-domain.

The immediate post entry events after the fusion of the infected virions are not clearly understood. However, it is clear that uncoating and disassembly of the mature viral core to release viral genetic material for further processing is critical for the HIV-1 life cycle. A number of studies involving Gag mutations have indicated that Gag may play a critical role in these early events in HIV-1 life cycle.

During HIV-1 assembly and morphogenesis, Gag organizes into two completely different arrangements, immature and mature forms. In case of immature form, Gag remains intact, whereas the mature form is composed of proteins cleaved by viral protease. The formation of this mature particle is essential for HIV-1 infectivity and the capsid protein obtained from the Gag cleavage product plays central role in forming the conical core of the virus that surrounds the viral genome. The capsid protein (CA, p24) is a hydrophobic protein consists of two domains, N-terminal domain (NTD, amino acids 1-145) and C-terminal domain (CTD, amino acids 146-231). These two domains are connected with a 5-amino acid linker and fold independently of each other. Although the exact nature of the CA-CA contacts and their interactions in immature particles are not fully known, in mature particles, the CA lattice has been modeled based on the structural studies and the image reconstruction by cryo-electron microscopy of pure mature virions and assembled virus-like particles. HIV-1 capsid plays crucial role in viral assembly, maturation and early post-entry steps. Mutations of the capsid in both NTD and CTD have been shown to lead to defects in viral assembly and release. In addition, the capsid has been shown as a dominant determinant of retrovirus infectivity in non-dividing cells.

The NTD of the HIV-1 capsid binds to cyclophylin A and is important for viral core formation; however, critical determinants of Gag oligomerization, essential for viral assembly and maturation, are located in the C-terminal domain of capsid. In addition, the CTD encompasses the most conserved segment of Gag known as the major homology region (MHR). Mutation of this conserved region causes severe defects in viral assembly and maturation. The isolated CTD of HIV-1 capsid forms a dimer in solution with the same affinity as the full-length capsid. It has been shown that CTD dimerization is the major driving force in Gag assembly, virus budding and maturation. Several structures of the CTD dimer have been reported, which provided critical information on the dimer interface. Mutation of the interface residues in the CTD monomer disrupts the dimer formation, impair capsid assembly and maturation and renders virus non-infectious.

Taken together, it is evident that capsid plays an important role in HIV-1 assembly and maturation and has been recognized as a potential target for developing new generation of drugs for AIDS therapy.

Protein-protein interactions play a key role in a range of biological processes such as antigen-antibody interaction, viral assembly, programmed cell death, cell differentiation and signal transduction. Therefore, controlling these interactions offers opportunities for developing novel therapeutic agents. However, inhibiting these processes by traditional drug discovery techniques may be complicated and challenging due to the shallow binding interfaces and relatively large interfacial areas involved in most protein-protein interactions. Until recently, it was believed to be virtually impossible to inhibit protein-protein interactions. However, this notion is now changing due to recent advances in this area. In addition, recent studies on crystallized antigen-antibody complexes have shown that only a limited number of residues from each protein partner are involved in mediating protein-protein interactions. These restricted areas at the binding interfaces are known as 'hot spots', small areas of bumps and holes that account for most of the protein interface's free energy of binding. Therefore it has been established that inhibitory molecules do not have to cover the entire binding interface to inhibit protein-protein interactions and that targeting these 'hot spots' may potently inhibit interprotein contacts.

Dimeric proteins provide a classical example of protein-protein interactions through surface recognition. There are several examples of competitive inhibitors of protein dimerization that exploited the structure of the protein interfaces. For example, interfacial peptides have been shown to inhibit dimerizaton of HIV-1 integrase, protease and reverse transcriptase. However, none of these peptides is clinically useful due to their lack of cell permeability.

SUMMARY OF THE INVENTION

Disclosed herein are cell-penetrating peptides useful as therapeutic agents against viruses, in particular the Human Immunodeficiency Virus 1 (HIV-1).

In one embodiment, disclosed herein are peptides comprising a sequence from 14 to 21 amino acids in length, wherein two of the amino acids are unnatural amino acids having either R or S stereochemistry at the α-carbon; wherein the α-carbon of the unnatural amino acids comprises a methyl group and an olefinic group, where the two olefinic groups of the unnatural amino acids are on the same side of the a-helix and are joined to form a cross-link between the two unnatural amino acids; wherein the sequence of the peptide comprises (Q/A)(E/A/K)(V/W)(E/K)NW(M/A)TETLL(V/K)(QAE) (SEQ ID NO:18); wherein the two unnatural amino acids replace two of the amino acids at any positions four amino acids apart or seven amino acids apart; and wherein the cross-link between the two unnatural amino acids is a C1-C10 alkyl, alkenyl, alkynyl, $(R1\text{-}K\text{-}R1)_n$, each of which is substituted with a 0-6 R2, wherein R1 is an alkyl, alkenyl or alkynyl, K is O, S, SO, SO2, CO, CONR4, or

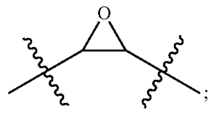 [SMILES: *C1OC1*]

;

R2 is a halo, C1-C10 alkyl, OR3, $N(R3)_2$, SR3 SOR3, $SO_2R3$, $CO_2R3$, R3, a fluorescent moiety or a radioisotope;

R3 is H or a C1-C10 alkyl;

R4 is H, alkyl or a therapeutic agent; and n is an integer from 1-4.

In another embodiment, the unnatural amino acid is (S)-α-2-(4'-pentenyl)alanine or (R)-α-2-(7'-octenyl)alanine. In another embodiment, unnatural amino acids replace the sixth and tenth amino acids of the peptide.

In yet another embodiment, the cross-link between the two unnatural amino acids comprises

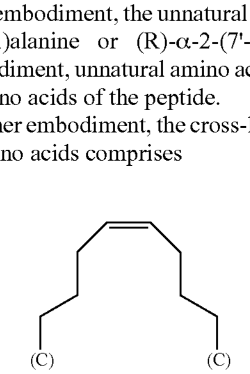

Or

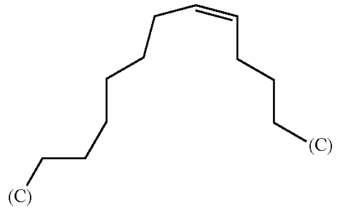

wherein the (C)s are the α-carbons of the unnatural amino acids.

In another embodiment, the peptide comprises an amino acid sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:12, SEQ ID NO:13, SEQ ID NO:14, SEQ ID NO:15, SEQ ID NO:16 and SEQ ID NO:17.

In one embodiment, a composition for treatment of a viral infection in a mammal is provided, the composition comprising an antiviral peptide having an amino acid sequence of at least a portion of a human immunodeficiency virus capsid protein, the peptide having substitutions at a first amino acid and a second amino acid wherein the peptide is cross-liked at the substitutions. In another embodiment, the first amino acid occurs at position (i) of the peptide and the second amino acid occurs at position (i+4) or (i+7) of the peptide. In another embodiment, the substitution comprises a non-natural amino acid such as (S)-α-2-(4'-pentenyl)alanine or (R)-α-2-(7'-octenyl)alanine.

In another embodiment, the composition comprises the peptide in a pharmaceutically acceptable carrier.

In one embodiment, a method of inhibiting replication of a human immunodeficiency virus in a cell is provided, the method comprising contacting the cell with a disclosed peptide in a dose sufficient to inhibit replication of the human immunodeficiency virus in the cell. In another embodiment, the cell is in a mammal infected with a human immunodeficiency virus. In another embodiment, the method comprises treating the mammal with at least one additional antiviral drug.

In one embodiment, a method of treating a mammal at risk for infection with a human immunodeficiency virus is provided comprising administering the disclosed peptide to the mammal in dose sufficient to inhibit replication of the human immunodeficiency virus.

In another embodiment, disclosed herein is the use of at least one disclosed peptide in the manufacture of a medicament for the treatment of a mammal infected with a human immunodeficiency virus.

In yet another embodiment, disclosed herein is the use at least one disclosed peptide in the manufacture of a medicament for the treatment of a mammal to reduce the risk of the mammal becoming infected with a human immunodeficiency virus.

BRIEF DESCRIPTION OF THE DRAWINGS

FIGS. 3A and 3D represent images of live cells (DIC); FIGS. 3B and 3D represent fluorescent images of the same field as in FIGS. 3A and 3C; and FIGS. 3C and 3F represent the combined images of FIGS. 3A and 3B, and 3C and 3D, respectively.

FIG. 4 depicts inhibition of in vitro assembly of mature-like particles by NYAD-201 as evidenced by electron microscope (EM) images of capsid (CA) proteins (50 μM) in the presence of no peptide (FIG. 4A), 0.25-molar equivalent of NYAD-201 peptide (FIG. 4B), 0.50-molar equivalent of NYAD-201 peptide (FIG. 4C), 1.0-molar equivalent of NYAD-201 peptide (FIG. 4D), 3.0-molar equivalent of NYAD-201 peptide (FIG. 4E) and 5.0-molar equivalent of NYAD-201 peptide (FIG. 4F).

FIG. 5 depicts electron microscopic analysis of HIV-1 virus-like particles produced in the absence (FIG. 5A) or presence (FIG. 5B) of 50 μM NYAD-201.

DETAILED DESCRIPTION OF THE INVENTION

Figure 1:
FIG. 1 depicts the amino acid sequences of selected peptides. Z=(R)-α-2-(7'-octenyl)alanine; X=(S)-α-2-(4'-pentenyl)alanine.
Figure 1:
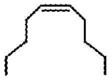
Figure 1:
Figure 1:
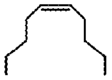
Figure 1:
Figure 1:
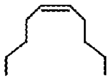
Figure 1:

Disclosed herein are cell-penetrating peptides useful as therapeutic agents against viruses, in particular the Human Immunodeficiency Virus 1 (HIV-1).

During HIV-1 assembly and morphogenesis, the structural protein, Gag, organizes into two completely different arrangements, immature and mature forms. In the immature form, Gag remains intact whereas in the mature form, the proteins are cleaved by viral protease. The formation of this mature particle is essential for HIV-1 infectivity and the capsid protein obtained from the Gag cleavage product plays a central role in forming the conical core of the virus that surrounds the viral genome. The capsid protein (CA, p24; SEQ ID NO:1) is a hydrophobic protein consisting of two domains, an N-terminal domain (NTD, amino acids 1-145) and a C-terminal domain (CTD, amino acids 146-231). These two domains are connected with a five amino acid linker and fold independently of each other. Although the exact nature of the capsid protein contacts and their interactions in immature particles are not fully known, in mature particles the CA lattice has been modeled. Mutations in both the NTD and CTD lead to defects in viral assembly, release and maturation. In addition, the capsid is a dominant determinant of retrovirus infectivity in non-dividing cells.

The NTD binds to cyclophilin A and is important for viral core formation. However, critical determinant of Gag oligomerization, essential for virus assembly, are located in the CTD. In addition, the CTD encompasses the most conserved segment of Gag known as the major homology region (MHR). Mutation of this conserved regions causes severe defects in viral assembly and maturation. The isolated CTD of HIV-1 forms a dimer in solution with the same affinity as the full-length protein. It has been shown that CTD dimerization is the major driving force in Gag assembly, virus budding and maturation. Several different three dimensional structures of CTD dimers are known and have provided information on the dimer interface. Mutation of amino acid residues in the interface region of the CTD monomer disrupts dimer formation, impairs capsid assembly and maturation and renders the virus non-infectious. Therefore, the CTD dimer is a potential target for anti-HIV-1 drugs.

HIV-1 capsid forms dimers in solution with low affinity ($K_d$=18 μM). The dimer interface has been mapped to the CTD helix II by x-ray structure analysis. Because the CTD dimer plays a critical role in HIV-1 assembly, the x-ray structures of the CTD dimer (PDB codes: 1a43 and 1a8o) has been extensively analyzed and a short a-helical segment (aa 175-195) from one monomer at the dimer interface region was selected as a starting point for designing antiviral that may competitively bind to one monomer of the CTD and prevent CTD dimerization. The biggest challenge of these short peptides is that they are normally unstructured in solution and will not penetrate cells. Since CTD dimer formation occurs within the cell, any potential drug seeking to interfere with dimer formation will necessarily have to enter the cell. Therefore, the present inventors determined that hydrocarbon stapling would stabilize the helical structure of the short peptides and would make them cell penetrating. These peptides bind to the monomeric CTD at the interface with a higher affinity than the partner monomer and they prevent capsid dimer formation, a necessary step in HIV-1 assembly and maturation.

A chemical approach, called hydrocarbon stapling, overcomes the tendency of short peptides to lose their critical three-dimensional structure—and their ability to function as desired—when removed from the context of the complete protein. This has been one of the greatest obstacles associated with using short peptides as therapeutic agents, and has hindered their legitimacy as pharmaceutical lead compounds. In this technique, α-methylated amino acids containing olefinic side chains of varying length are introduced at the (i) and either (i+4) or (i+7) positions of the peptide sequence and then cyclized by olefin metathesis. As used herein, (i) refers to a reference amino acid residue and the term (i+x) refers to an amino acid x residues from the (i) amino acid. By making the peptides more resistant to degradation and enabling their cellular uptake, the hydrocarbon staple overcomes some of the classic shortcomings of peptide therapeutics. Stapled peptides retain their natural shape, are resistant to degradation, and can enter and exert their intended function in cells.

Hydrocarbon stapling refers to a process of replacing non-natural amino acids for natural amino acids in selected positions such that the non-natural amino acids include hydrocarbons that can be cross-linked to one another. The "staple" provides a tether between the non-natural amino acids which constrains the secondary structure of the peptide.

The present disclosure is drawn to compositions for the treatment of viral infections in a mammal comprising cell-penetrating peptides. The cell-penetrating peptides comprise an amino acid sequence of at least a portion of am HIV-1 viral capsid protein, the peptide having substitutions at a first amino acid and a second amino acid wherein the peptide is cross-linked at the substitutions.

In one embodiment, disclosed herein are peptides comprising sequences from 14 to 21 amino acids in length, wherein two of the amino acids are unnatural amino acids having either R or S stereochemistry at the α-carbon; wherein the α-carbon of the unnatural amino acids comprises a methyl group and an olefinic group, where the two olefinic groups of the unnatural amino acids are on the same side of the a-helix and are joined to form a cross-link between the two unnatural amino acids; wherein the sequence of the peptide comprises (Q/A)(E/A/K)(V/W)(E/K)NW(M/A)TETLL(V/K)(QAE) (SEQ ID NO:18); wherein the two unnatural amino acids replace two of the amino acids at any positions four amino acids apart or seven amino acids apart; and wherein the cross-link between the two unnatural amino acids is a C1-C10 alkyl, alkenyl, alkynyl, $(R1\text{-}K\text{-}R1)_n$, each of which is substituted with a 0-6 R2, wherein R1 is an alkyl, alkenyl or alkynyl, K is O, S, SO, $SO_2$, CO, CONR4, or

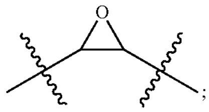 [SMILES: *C1OC1*]

;

R2 is a halo, C1-C10 alkyl, OR3, $N(R3)_2$, SR3 SOR3, $SO_2R3$, $CO_2R3$, R3, a fluorescent moiety or a radioisotope;

R3 is H or a C1-C10 alkyl;

R4 is H, alkyl or a therapeutic agent; and n is an integer from 1-4.

In the above formula, it should be understood that amino acids are only represented by letters within parentheses followed by "wherein the sequence of the amino acids of the peptide comprises". The R's outside of those parentheses (R1, R2, R3, and R4) and the K in "(R1-K-R1)" would be understood to represent variables that are subsequently defined, and the H, C, S outside of those parentheses would be understood to represent the atoms hydrogen, carbon and sulfur, respectively.

In other embodiments, the peptide includes additional amino acids at either the c-terminus or N-terminus of (Q/A)(E/A/K)(V/W)(E/K)NW(M/A)TETLL(V/K)(QAE) (SEQ ID NO:18).

It is contemplated that the disclosed peptides also encompass future variations in known procedures for stabilizing α-helices. For example, it is believed that the methyl group of the unnatural amino acids could be substituted with another small (e.g., C1-05) alkyl, alkenyl, or alkynyl without affecting the activity of the peptide in vitro or in vivo, or the ability of the cross-link to stabilize the peptide and increase its α-helicity.

As used herein, the designation of an amino acid residue in the instant peptides as more than one amino acid (using the common one-letter amino acid code) in parenthesis with a slash between the amino acids, mean that any of the indicated amino acids, or mimetics thereof (unless specifically excluded), could occupy that residue. For example, (I/L/V)(T/S/A/V/C) means that the first residue can be any one of isoleucine, leucine, or valine, and the second residue can be any one of threonine, serine, alanine, valine, or cysteine, or mimetics.

As used herein, a mimetic or peptidomimetic is a compound that is capable of mimicking a natural parent amino acid in a protein, in that the substitution of the peptidomimetic for the natural amino acid does not affect the activity of the protein. Proteins comprising peptidomimetics are generally not substrates of proteases and are likely to be active in vivo for a longer period of time as compared to the natural proteins. In addition, they could be less antigenic and show an overall higher bioavailability. The skilled artisan would understand that design and synthesis of peptidomimetics that could substitute for amino acids of any particular peptide (such as the peptides of this invention) would not require undue experimentation. Nonlimiting examples of mimetics useful for this invention include D-amino acids and constrained amino acids such as norleucine, or 2-aminoisobutyric acid. It is also within the confines of the present invention that amino acids in the peptide sequence can be substituted with amino acids having a propensity to form alpha helices.

Each peptide of the present disclosure can include the addition of one or more chemical groups at specific amino acid(s) and/or at the amino end and/or at carboxy end, in order to enhance the stability, reactivity and/or solubility of the peptides. For example, hydrophobic groups such as carbobenzoyl, dansyl, acetyl, a t-butyloxycarbonyl group, or a 9-fluorenylmethyoxycarbonyl group may be added to the amino terminal end of the peptide. In another example, the hydrophobic group, t-butyloxycarbonyl, or p-nitrobenzyl ester group, or a hydrophilic group such as 1-5 lysines may be added to the carboxy terminal end of the peptide. Techniques for introducing such modifications are well known to those of skill in the art.

The peptides of present disclosure may be in the form of any pharmaceutically acceptable salt. Acid addition salts of the disclosed compounds are prepared in a suitable solvent from the peptide and an excess of an acid, such as hydrochloric, hydrobromic, sulfuric, phosphoric, acetic, trifluoroacetic, maleic, succinic or methanesulfonic. Where these peptides include an acidic moiety, suitable pharmaceutically acceptable salts may include alkali metal salts, such as sodium or potassium salts, or alkaline earth metal salts, such as calcium or magnesium salts. A salt of the peptide in which the amino terminus is H and the carboxy terminus is NH2 is preferred. The scope of the present disclosure also includes the peptides in free acid form.

The amino acid residues for the disclosed include conservative substitutions. For example, conservative amino acid changes may be made, which although they alter the primary sequence of the protein or peptide, do not normally alter its function. Conservative amino acid substitutions typically include substitutions within the following groups: glycine and alanine; valine, isoleucine and leucine; aspartic acid and glutamic acid; asparagine and glutamine; serine and threonine; lysine and arginine; and phenylalanine and tyrosine.

The non-natural amino acids suitable for use in hydrocarbon stapling have either an R or S stereochemistry at the α-carbon and wherein the α-carbon of the non-natural amino acids comprises a methyl group and an olefinic group, where the two olefinic groups of the non-natural amino acids are on the same side of the a-helix and have the ability to form a cross-link between two non-natural amino acids.

In one embodiment, the cross-link between the two unnatural amino acids is

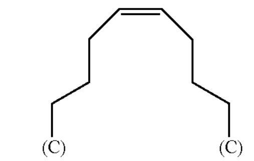

Or

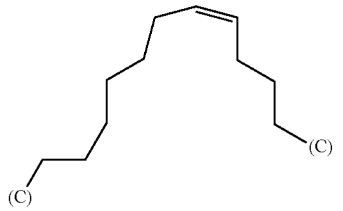

wherein the (C)s are the α-carbons of the unnatural amino acids.

Without being bound to any particular mechanism, it is believed that the peptide binds to the capsid domain of the HIV gag protein, preventing uncoating, viral assembly and maturation and thus replication. As such, the disclosed peptides are expected to bind and inhibit replication of any capsid-containing virus. Thus, preferred peptides can inhibit replication of a capsid-containing virus in a cell. Examples of capsid-containing viruses include the Retroviridae, including lentiviruses, such as HIV; Togaviridae including rubella virus; Picornaviridae such as enteroviruses, poliovirus, rhinovirus and hepatitis A virus; Orthomyxoviridae such as influenza virus; Paramyxoviridae such as paramyxoviruses; Herpesviridae such as herpes viruses and cytomegaloviruses; Hepnaviridae such as hepatitis B viruses; Flaviviridae such as flavivirus, hepatitis C virus, tick borne encephalitis, yellow fever and dengue fever viruses; Coronaviridae such as coronaviruses including SARS virus and toroviruses; Filoviridae such as Ebola and Marburg viruses; Bunyaviridae such as hantaviruses and arenaviruses.

The capsid-containing virus is preferably a retrovirus, e.g., HIV, HTLV-1, 2 and 3, a feline immunodeficiency virus, a bovine immunodeficiency virus, a simian immunodeficiency virus, a feline sarcoma or leukemia virus, or a bovine leucosis virus.

More preferably, the peptide inhibits replication of a lentivirus. In the certain embodiments, the peptide can inhibit replication of an HIV. It is expected that the peptides could inhibit any strain of HIV, including HIV-I and HIV-2, since the Examples show that the peptide described above inhibits a wide range of HIV isolates (Table 2).

In one embodiment, the NYAD-201 peptide (SEQ ID NO:4) was generated by deleting three amino acids from both N- and C-termini and replacing two natural amino acids at the 6(i) and 10(1+4) positions of the dimer interface sequence (FIG. 1: EQASQEVKNWMTETLLVQNAN, SEQ ID NO:2) by a non-natural amino acid (S)-α-2-(4'-pentenyl)alanine. The four N- and C-terminal residues (EQAS and QNAN) have also been substituted with one alanine each. The $6^{th}$ and $10^{th}$ residues were selected based on the x-ray crystal structures of CTD dimer interface of the capsid (PDB code: 1a43 and 1a8o). They were located to the opposite side of the dimer interface. Stapling residues at the $6^{th}$ and $10^{th}$ positions is not anticipated to affect the binding of the modified peptides to the hydrophobic pocket; it is instead anticipated to enhance the α-helicity and cell permeability of the peptide. Peptide NYAD-202 (SEQ ID NO:5) was obtained by substituting the $3^{rd}$ residue of NYAD-201 to alanine. NYAD-203 (SEQ ID NO:6), a soluble analog of NYAD-201, was also synthesized by the addition of three lysines at the C-terminal end of NYAD-201. In addition, as part of the structure-activity relationship studies (SAR), a variety of stapled peptides were synthesized in which certain amino acids were modified, additional amino acids were added, especially to the C-terminal of the sequence, and still other amino acids were moved such that the stapling side was moved towards the C-terminus (NYAD-218, SEQ ID NO:12). The modifications have been shown in the exemplary peptides in FIG. 1.

In another embodiment, NYAD-221 (SEQ ID NO:15) was generated by replacing the natural amino acids at the 6(i) and 13(i+7) positions of SEQ ID NO:19 by non-natural amino acids (R)-α-2-(7'-octenyl)alanine and (S)-α-2-(4'-pentenyl) alanine, respectively. The $6^{th}$ and $13^{th}$ residues have been selected based on the same rationale as described before for NYAD-201. NYAD-222 (SEQ ID NO:16) was similarly made but several amino acids have been substituted by other natural amino acids and the C-terminal was extended by one additional amino acid (FIG. 1).

TABLE 1

Exemplary peptides

| SEQ ID NO. | Sequence | Description |
|---|---|---|
| 18 | (Q/A)(E/A/K)(V/W)(E/K)NW(M/A)TETLL(V/K)(QAE) | Antiviral peptide backbone sequence |
| 2 | EAQSQEVKNWMTETLLVQNAN | Dimer interface sequence |
| 3 | AQEVKNWMTETLLVA | NYAD-209 |
| 4 | AQEVKXWMTXTLLVA | NYAD-201 |
| 5 | AQAVKXWMTXTLLVA | NYAD-202 |
| 6 | AQEVKXWMTXTLLVAKKK | NYAD-203 |
| 7 | AKVEXWMTXTLLVA | NYAD-210 |
| 8 | AQAVKXWMTXTLLVENA | NYAD-212 |
| 9 | AQAVKXWMTXTLLKANAE | NYAD-214 |

TABLE 1 -continued

Exemplary peptides

| SEQ ID NO. | Sequence | Description |
|---|---|---|
| 10 | EQLVWXKMTXALAVT | NYAD-215 |
| 11 | FITC-β-Ala-AQEVKNWMTETLLVA | NYAD-216 |
| 12 | AQAVKNWMTXTLLXA | NYAD-218 |
| 13 | AQAWKXWATXTLLVAE | NYAD-219 |
| 14 | AQAVKXWMEXTLKVAE | NYAD-220 |
| 15 | AQAVKZWMTETLXVA | NYAD-221 |
| 16 | AQAWKZWATETLXVAN | NYAD-222 |
| 17 | IAQAKVEXWMTXTLLVAN | NYAD-223 |

Z = (R)-α-2-(7'-octenyl)alanine;
X = (S)-α-2-(4'-pentenyl)alanine

The present disclosure is also directed to pharmaceutical compositions comprising the above-described peptides that can inhibit uncoating, assembly and maturation of a capsid-containing virus, in a pharmaceutically acceptable carrier.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mardenti, J. and Chappell, W. “The use of interspecies scaling in toxicokinetics” In Toxicokinetics and New Drug Development, Yacobi et al, Eds., Pergamon Press, New York 1989, pp. 42-96. The term “therapeutically effective” amount as used herein refers to the amount needed to perform the particular treatment for a disease such as, for example, an infectious disease. “Treatment” refers to both therapeutic treatment and prophylactic or preventative measures, wherein the object is to prevent or slow down (lessen) the targeted pathologic condition or disease. Those in need of treatment include those already with the disease as well as those prone to have the disease or those in whom the disease is to be prevented. In one embodiment, the disease is present. In another embodiment, the life of a cell or an individual is prolonged due to the methods described herein.

The above-described compounds can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, nasal, lingual, sublingual, buccal and intrabuccal administration can be made without undue experimentation by means well known in the art, for example with an inert diluent or with an pharmaceutically acceptable carrier. The compositions are enclosed in gelatin capsules or compressed into tablets. For the purpose of oral therapeutic administration, the pharmaceutical compositions may be incorporated with excipients and used in the form of tablets, troches, capsules, elixirs, suspensions, syrups, wafers, chewing gums and the like. A “pharmaceutically acceptable carrier” means any of the standard pharmaceutical carriers. Examples of suitable carriers are well known in the art and may include but are not limited to any of the standard pharmaceutical carriers like phosphate buffered saline solutions, phosphate buffered saline containing Polysorb 80, water, emulsions such as oil/water emulsion, and various types of wetting agents. Other carriers may also include sterile solutions, tablets, coated tablets, and capsules. Typically such carriers contain excipients like starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

Tablets, pills, capsules, troches and the like may also contain binders, excipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compounds can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the compound, in a pharmaceutical composition, into the rectum or large intestine. This can be accomplished using suppositories, enemas, gels, creams, tablets, and the like. Suppository formulations can easily be made by methods known in the art. Similarly, vaginal administration forms comprising suppositories, gels, douches, creams, tablet, rings and the like can be formulated. The composition may be intended for rectal or vaginal administration, in the form, e.g., of a suppository which will melt in the rectum and release the drug. The composition for rectal or vaginal administration may contain an oleaginous base as a suitable nonirritating excipient. Such bases include, without limitation, lanolin, cocoa butter and polyethylene glycol. Low-melting waxes are preferred for the preparation of a suppository, where mixtures of fatty acid glycerides and/or cocoa butter are suitable waxes. The waxes may be melted, and the cyclohexylamine compound is dispersed homogeneously therein by stirring. The molten homogeneous mixture is then poured into convenient sized molds, allowed to cool and thereby solidify.

The disclosed composition intended for topical administration may suitably comprise a solution, emulsion, ointment, cream or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration.

Transdermal administration includes percutaneous absorption of the composition through the skin. Transdermal formulations include patches, iontophoresis devices, ointments, creams, gels, salves and the like.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule or cachet The disclosure is additionally directed to methods of inhibiting replication of the capsid-containing virus in a cell. The methods comprise contacting the cell with the above-described peptides that can inhibit a capsid-containing virus, in a manner sufficient to inhibit replication of the capsid-containing virus in the cell.

These methods are useful with any capsid-containing virus. Preferably the virus is a retrovirus, more preferably a lentivirus and most preferably an HIV.

Any prokaryotic, eukaryotic or archaea cell infected with a capsid-containing virus can be treated with the invention peptides. The method can utilize cells in culture (e.g., as in Examples), or preferably in a live multicellular organism, including any plants or animals. More preferably, the cell is part of a live vertebrate infected with the capsid-containing virus. Even more preferably, the cell is in a mammal infected with the capsid-containing virus. Still more preferably, the mammal is a human, most preferably infected with HIV.

Where the virus is in a live mammal, it is contemplated that the present methods could be used in conjunction with at least one other antiviral treatment, for example any antiviral treatment, or combination thereof, used against HIV.

The disclosure is further directed to methods of treating a mammal infected with a capsid-containing virus. The methods comprise administering the above-described pharmaceutical composition to the mammal in a manner sufficient to treat the mammal. Preferably, the mammal is a human.

Some applications of these methods comprise treating a fetus in utero having a mother that is infected with the virus to reduce the risk of passing the virus to the fetus in utero or to the baby during delivery.

It is also contemplated that the present methods could be used in conjunction with at least one other antiviral treatment, for example any antiviral treatment, or combination thereof, used against HIV, or any preventative antiviral treatment, including vaccination.

Further, the disclosure is directed to methods of making any of the above-described peptides. The methods comprise sequentially coupling the amino acids, then joining the two olefinic groups of the unnatural amino acids together using olefin metathesis. These methods are described in, e.g., United States Patent Application Publication 2006/0008848 A1 and PCT Patent Application Publication WO 2005/044839 A2, both of which are incorporated by reference herein for all they disclose regarding hydrocarbon stapling of peptides. Preferably, the amino acids are coupled using solid phase synthesis.

Also directed is the use any of the above-described peptides that inhibit uncoating, assembly and maturation of a capsid-containing virus for the manufacture of a medicament for the treatment of a mammal infected with a capsid-containing virus. Additionally, the use any of the above-described peptides that can inhibit assembly of a capsid-containing virus for the manufacture of a medicament for the treatment of a mammal to reduce the risk of the mammal becoming infected with a capsid-containing virus.

Also, the disclosure is directed to the use of the above-described pharmaceutical compositions for the treatment of a mammal infected with a capsid-containing virus. The disclosure is additionally directed to the use of the above-described compositions for the treatment of a mammal at risk for infection with a capsid-containing virus.

The compositions of the present disclosure may be administered in a therapeutically effective amount, according to an appropriate dosing regiment. As understood by a skilled artisan, the exact amount required may vary from subject to subject, depending on the subject's species, age and general condition, the severity of the infection, the particular agent(s) and the mode of administration. In some embodiments, about 0.001 mg/kg to about 50 mg/kg, of the composition based on the subject's body weight is administered, one or more times a day, to obtain the desired therapeutic effect. In other embodiments, about 1 mg/kg to about 25 mg/kg, of the composition based on the subject's body weight is administered, one or more times a day, to obtain the desired therapeutic effect.

The total daily dosage of the compositions will be determined by the attending physician within the scope of sound medical judgment. The specific therapeutically effective dose level for any particular patient or subject will depend upon a variety of factors including the disorder being treated and the severity of the disorder; the activity of the specific compound employed; the specific composition employed; the age, body weight, general health, sex and diet of the patient or subject; the time of administration, route of administration, and rate of excretion of the specific compound employed; the duration of the treatment; drugs used in combination or coincidental with the specific compound employed, and other factors well known in the medical arts.

The disclosed compositions may also be employed in combination therapies. That is, the compositions presently disclosed can be administered concurrently with, prior to, or subsequent to, one or more other desired compositions, therapeutics, treatments or medical procedures. The particular combination of therapies administered will be determined by the attending physician and will take into account compatibility of the treatments and the desired therapeutic effect to be achieved. It will be appreciated that therapeutically active agents utilized in combination may be administered together in a single composition, treatment or procedure, or alternatively may be administered separately.

For example, the disclosed compositions may be administered in combination with one or more other HIV inhibitors including, for example, but not limited to, one or more nucleoside/nucleotide reverse transcriptase inhibitors (NRTIs), non-nucleoside reverse transcriptase inhibitors (NNRTIs), protease inhibitors (PIs), fusion inhibitors, integrase inhibitors, chemokine receptor (CXCR4, CCR5) inhibitors and/or hydroxyurea.

Nucleoside reverse transcriptase inhibitors, include but are not limited to, Abacavir (ABC; Ziagen®), didanosine (dideoxyinosine (ddI); Videx®), lamivudine (3TC; Epivir®), stavudine (d4T; Zerit®, Zerit XR®), zalcitabine (dideoxycytidine (ddC); Hivid®), zidovudine (ZDV, formerly known as azidothymidine (AZT); Retrovir®), abacavir, zidovudine, and lamivudine (Trizivir®), zidovudine and lamivudine (Combivir®), and emtricitabine (Emtriva®). Nucleotide reverse transcriptase inhibitors include tenofovir disoproxil fumarate (Viread®). Non-nucleoside reverse transcriptase inhibitors for HIV include, but are not limited to, nevirapine (Viramune®), delavirdine mesylate (Rescriptor®), and efavirenz (Sustiva®).

Protease inhibitors (PIs) include amprenavir (Agenerase®), saquinavir mesylate (Fortovase®, Invirase®), ritonavir (Norvir®), indinavir sulfate (Crixivan®), nelfmavir mesylate (Viracept®), lopinavir and ritonavir (Kaletra®), atazanavir (Reyataz®), and fosamprenavir (Lexiva®). Atazanavir and fosamprenavir (Lexiva) are new protease inhibitors that were recently approved by the U.S. Food and Drug Administration (FDA) for treating HIV-1 infection (see atazanavir (Reyataz) and emtricitabine (Emtriva) for HIV infection, Medical Letter on Drugs and Therapeutics, available online at www.medletter.com; U.S. Department of Health and Human Services (2003). Guidelines for the Use of Antiretroviral Agents in HIV-infected Adults and Adolescents; available online at aidsinfo.nih.gov/guidelines.

A fusion/entry inhibitor attaches to the outside of a CD4+ cell (a type of white blood cell) or coreceptors such as CCR5 and CXCR4 or to the viral membrane proteins, such as gp41 and gp120. Fusion/entry inhibitors prevent fusion between the virus and the cell from occurring or entry of the virus to the cells and therefore, prevent HIV infection and multiplication. Fusion/entry inhibitors include, but are not limited to, enfuvirtide (Fuzeon®), Lalezari et al., New England J. Med., 348:2175-2185 (2003); and maraviroc (Selzentry®, Pfizer).

An integrase inhibitor blocks the action of integrase, preventing HIV-1 genetic material from integrating into the host DNA, and thereby stopping viral replication. Integrase inhibitors include, but are not limited to, raltegravir (Isentress®, Merck); and elvitegravir (GS 9137, Gilead Sciences).

Alternatively or additionally, the compositions disclosed herein may be administered in combination with one or more anti-infective agents (e.g., antibiotics, etc.), pain relievers, or other agents intended to address symptoms of one or more diseases, disorders, or conditions commonly found in immunocompromised individuals but not directly caused by HIV.

EXAMPLES

Example 1

Synthesis of Stapled Peptides

Asymmetric synthesis of (S)-Fmoc-2-(4'-pentenyl)alanine and (R)-Fmoc-2-(7'-octenyl)alanine were conducted with the Ala-Ni(II)-BPB-complex method. NYAD-201 (also known as D-201) was derived from the dimer interface sequence (FIG. 1: EQASQEVKNWMTETLLVQNAN, SEQ ID NO:2) by replacing the amino acid serine in position 1 and glutamine in position 15 with alanine and replacing two natural amino acids at the 6 (i) and 10 (i+4) positions of the sequence by the non-natural amino acid (S)-Fmoc-2-(4'-pentenyl)alanine (NYAD-201, SEQ ID NO:4) and was synthesized by following the method described below. The rationale for selecting the $6^{th}$ and $10^{th}$ residues of the above sequence was based on the x-ray crystal structure of dimeric CTD of capsid. The original sequence of NYAD-201 adapts a helical structure in the capsid. Further structural analysis revealed that residues 6 (N) and 10 (E) are located on the opposite side of the dimer interface. Stapling residues in these positions should not affect the binding of the modified peptide to the dimer interface; in fact it can enhance the a-helicity and cell permeability of the peptide. NYAD-202 (also known as D-202) (SEQ ID NO:5) was designed by replacing the $3^{rd}$ amino acid of SEQ ID NO:4 with alanine and stapling at the same position as NYAD-201. A soluble analog of NYAD-201, NYAD-203 (also known as D-203) (SEQ ID NO:6), was designed by adding three lysines at the C-terminal of NYAD-202 (FIG. 1). NYAD-221 (SEQ ID NO:15) and NYAD-222 (SEQ ID NO:16) were designed by replacing two natural amino acids at 6(i) and 13(1+7) positions with two unnatural amino acids, (R)-Fmoc-2-(7'-octenyl)alanine and (S)-Fmoc-2-(4'-pentenyl)alanine, respectively. These peptides were synthesized manually by Fmoc solid phase synthesis using Rink amide MBHA resin (0.33 mmol/g). For the normal amino acids, the couplings were performed with a 4-fold excess of amino acids. Fmoc-amino acids were activated using a ratio of 1:1:1:2 for Fmoc-amino acid:HBTU:HOBt:DIEA. For (S)-Fmoc-2-(2'-pentenyl)alanine, the coupling was performed with a 2-fold excess of amino acids, which was activated with DIC:HOAt (1:1). For peptide olefin metathesis, the peptide resin with N-terminus protected by an Fmoc group was treated with degassed 1,2-dichloroethane containing the Grubbs catalyst, bis(tricyclohexylphosphine)benzylidineruthenium(IV) dichloride (10 mM), at room temperature for 2 hr, and the reaction was repeated once for completion. After de-Fmoc, the resin-bound peptide was cleaved using standard protocols (95% TFA, 2.5% water, 2.5% TIS). The cleaved peptide was purified by RP-HPLC using 0.1% (v/v) TFA/water and 0.1% (v/v) TFA/acetonitrile, and its purity and mass were confirmed by mass spectroscopy.

The circular dichroism (CD) spectrum of NYAD-201 and NYAD-209 (SEQ ID NO:3) was obtained on a Jasco J-715 Spectropolarimeter (Jasco Inc, Japan) at 20° C. using the standard measurement parameters in Tris-HCl buffer (20 mM Tris, pH8.0) in the presence of 15% (vol/vol) acetonitrile at a final concentration of 250 μM. In all the samples, the final concentrations of peptides and salt were always the same, and the spectra were corrected by subtracting the CD spectra of the appropriate reference solvent.

Figure 2:
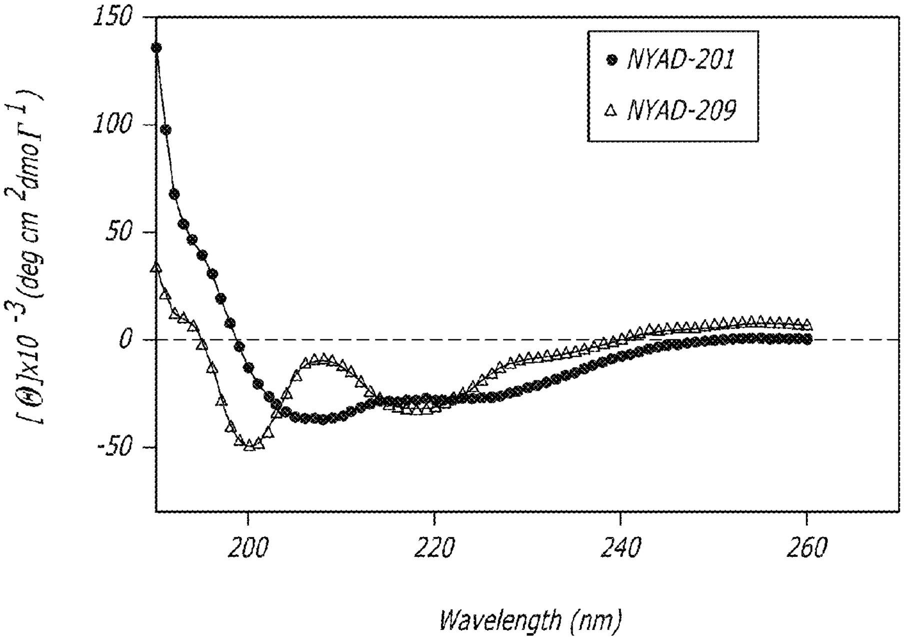
FIG. 2 depicts the circular dichroism (CD) spectra of NYAD-201 and NYAD-209.

Circular dichroism was used to characterize the secondary structure of NYAD-201 and its linear analog, NYAD-209, in the uncomplexed state in solution. The CD spectrum of NYAD-201 showed distinct minima at both 222 and 208 nm indicative of an α-helical structure (FIG. 2). Hydrocarbon stapled peptides prefer an a-helical state in the solution. However, the linear peptide, NYAD-209 showed no such distinct minima; therefore, this peptide does not exist as a-helical structure in solution.

Example 2

Assessment of Cell Penetration of NYAD-201

A confocal microscopic study was performed to show conclusively that the constrained stapled peptide, NYAD-201, penetrated the cell membrane and taken up by the cells whereas the linear analog, termed NYAD-209, did not penetrate.

Figure 3:
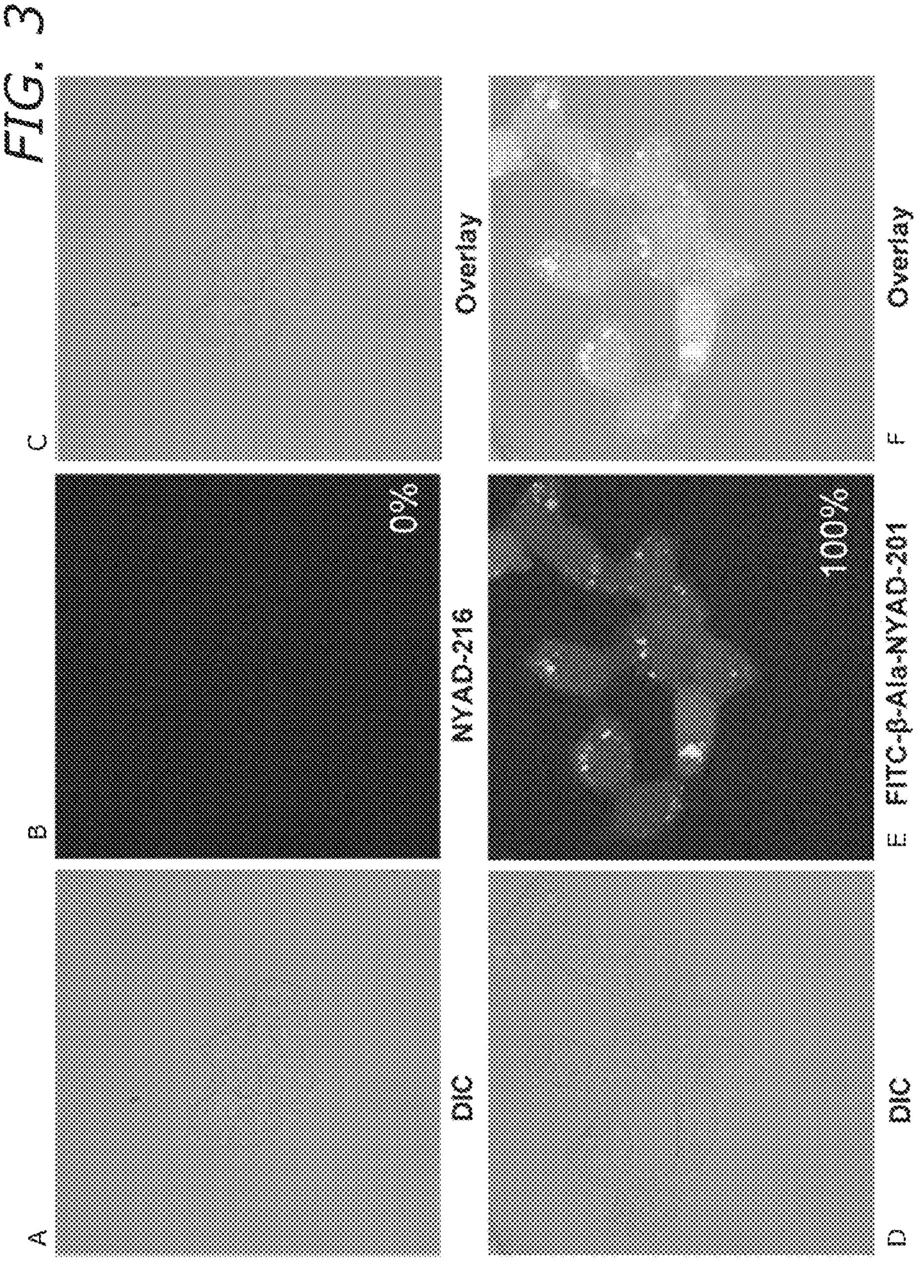
FIG. 3 depicts the cell penetration of NYAD-216 (FIGS. 3A-3C) and NYAD-201 (FIGS. 3D-3F).

Two type of cells, 293T (human embryonic kidney 293 cells) and MT2 (human lymphoid cells) were seeded in the 4-well chamber plates and incubated with FITC-conjugated peptides (FITC-derivatized NYAD-209 is designated NYAD-216, see FIG. 1) as described above in serum-free medium for 4 hours or/and additional 16 hours in the complete medium containing serum. After 3 washes with 1× PBS, live cells were examined and imaged under confocal microscope (Zeiss). As shown in FIG. 3, the NYAD-201 penetrated the cell membrane and was taken up by the cells, while the linear peptide (NYAD-209) did not penetrate.

Example 3

Electron Microscopy to Study Inhibition of In Vitro Assembly

In vitro assembly was studied in both a cell-free and a cell based system. The cell-free systems were set up as previously described (Huseby et al., J Biol Chem 280:17664-17670, 2005; Ganser-Pornillos et al., J Virol 78:2545-2552, 2004; and Gross et al., Eur J Biochem 249:592-600,1997) with minor modifications. Fifty millimolar $Na_2HPO_4$, pH 8.0 was used as the dialysis buffer. The buffer used for assembly studies also contained 1.2 M NaCl and 500-Da-MWCO dialysis tubes (Spectra/Por) were used for the dialysis of peptides. Briefly, stock proteins were adjusted to the appropriate concentration (50 μM for CA proteins) in $Na_2HPO_4$ buffer at pH 8.0. After incubation with varied doses of NYAD-201 for 30 min at 4° C., the samples were dialyzed overnight at 4° C. in $Na_2HPO_4$ buffer at pH 8.0 containing 1.2 M NaCl. Negative staining was used to check the assembly. Carbon-coated copper grids (200 mesh size; EM Sciences) were treated with 20 μl of poly-L-lysine (1 mg/ml; Sigma) for 2 min. Twenty microliters of reaction solution was placed onto the grid for 2 min. Spotted grids were then stained with 30 μl of uranyl acetate solution for 2 min. Excess stain was removed, and the grids were air-dried. Specimens were examined with a Philips EM410 electron microscope.

Purified CA protein was expressed and tube-shaped particles were obtained (FIG. 4). Treatment with NYAD-201 resulted in dose-dependent disruption of the mature-like particles. After incubation with 0.25- and 0.5-fold molar equivalents of NYAD-201, the integrity of tube-like particles was greatly damaged (FIG. 4). After incubation with 1-, 3- and 5-fold molar equivalents of NYAD-201, the assembly of tube-shaped particles were completely blocked (FIG. 4).

In the cell-based system, the impact of NYAD-201 on virus-like particle (VLP) release and morphology was analyzed by electron microscopy one day post-transfection with plasmid encoding Gag-Pol. Forty thousand 293T cells were seeded per well in a 6-well plate on the day before transfection. Cells were washed twice 4 hr post-transfection and incubated with complete culture medium in the presence or absence of NYAD-201 at different concentrations for another 20 hr. The cells were then fixed in 3% glutaraldehyde in 100 mM sodium cacodylate for 1 hr and post-fixed in 1% $OsO_4$ in 100 mM sodium cacodylate for another 1 hr. Specimens were then dehydrated through graded series of ethanol solutions and embedded in EPON media. After staining with uranyl acetate and lead citrate, ultra-thin sections were examined under a Philips EM410 electron microscope at 80 Kv.

In the case of untreated cells transfected with a Gag-Pol expression vector, a large number of mature particles containing electron-dense core structures were found (FIG. 5). When Gag-Pol expressing cells were treated with 50 μM NYAD-201, formation of electron-dense core structures was markedly inhibited (FIG. 5). These data confirm that NYAD-201 targets capsid and impairs proper particle assembly and maturation in Gag-Pol expressing cells.

Example 4

Inhibition of HIV-1 Infectivity

The inhibitory activity of NYAD-201, and related stapled peptides on infection by laboratory-adapted HIV-1 strains was determined as previously described (Jiang et al. J Exp. Med 174:1557-1563, 1991) with minor modifications. Azidothymidine (AZT) was used as a positive control in the infectivity assays. In brief, $1\times10^4$ MT-2 cells were infected with HIV-1 at 100 $TCID_{50}$ (50% tissue culture infective dose) (0.01 MOI [multiplicity of infection]) in 200 μl RPMI 1640 medium containing 10% FBS in the presence or absence of peptides at graded concentrations overnight. The culture supernatants were then removed and fresh media containing freshly prepared test peptide were added. On the fourth day post-infection, 100 μl of culture supernatants were collected from each well, mixed with equal volume of 5% Triton X-100 and tested for p24 antigen by ELISA.

Figure 6:
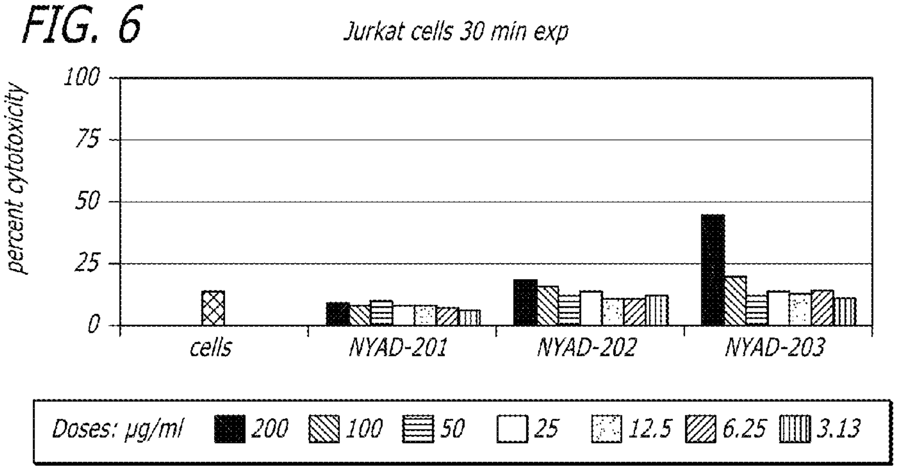
FIG. 6 depicts cytotoxicity of peptides NYAD-201, NYAD-202 and NYAD-203 in Jurkat cells after 30 min of exposure.

The inhibitory activity of peptides on infection by primary HIV-1 isolates was determined as previously described (Jiang et al., Antimicrob. Agents Chemother. 48:4349-4359, 2004). Peripheral blood mononuclear cells (PBMCs) were isolated from the blood of healthy donors at the New York Blood Center by standard density gradient centrifugation using Histopaque-1077 (Sigma-Aldrich). The cells were cultured at 37° C. for 2 hr. Nonadherent cells were collected and resuspended at $5\times10^6$ cells/ml RPMI-1640 medium containing 10% FBS, 5 μg/ml PHA, and 100 U/ml IL-2 (Sigma-Aldrich), followed by incubation at 37° C. for 3 days. The PHA-stimulated cells ($5\times10^4$ cells/well) were infected with primary HIV-1 isolates at 500 $TCID_{50}$ (0.01 MOI) in the absence or presence of peptide inhibitor at graded concentrations. Culture media were changed every 3 days and replaced with fresh media containing freshly prepared inhibitor. The supernatants were collected 7 days post-infection and tested for p24 antigen by ELISA (FIG. 6). The percent inhibition of p24 production, $IC_{50}$ and $IC_{90}$ values were calculated by the GraphPad Prism software (GraphPad Software Inc.).

Since NYAD-201 showed inhibition of mature-like particle assemblies in cell-free as well as cell-based assembly systems, NYAD-201 and related stapled peptides were tested for anti-HIV-1 activity in a cell-based assay using HIV-1 IIIB strains (Table 2). In addition, NYAD-201, NYAD-202 and NYAD-203 were also tested using several laboratory-adapted and primary isolates in MT-2 cells and PBMC (peripheral blood mononuclear cells), respectively. The inhibition of p24 production in MT-2 cells by NYAD-201 and its analogs were measured over a range of concentrations and the concentration required to inhibit 50% ($IC_{50}$) of the p24 production was calculated. The results in Tables 2 and 3 indicate that these peptides efficiently inhibited a broad range of HIV-1 strains, representing different subtypes, which use R5, X4 or R5X4 co-receptors. NYAD-201 and its analogs inhibited the laboratory strains with low μM potency ($IC_{50}$~2-8 μM), and both R5- and X4-tropic viruses were inhibited with similar potency. One X4-tropic RT-resistant (AZT-R) and one PR-resistant strain were also tested in MT-2 cells and showed significant inhibition.

NYAD-201, NYAD-202 and NYAD-203 were also tested against a set of primary HIV-1 isolates in PBMC representing mostly group M and one from group O with diverse coreceptor usage. They showed inhibition against all primary isolates tested including the isolate from group O (Table 3). The inhibitory activities of the peptides against this diverse range of primary isolates were similar, indicating its effectiveness against a wide range of HIV-1 isolates.

Example 5

Cytotoxicity of Cell Penetrating Peptides

Cytotoxicity of peptides in MT-2 cells and PBMC was measured by the XTT [(sodium 3'-(1-(phenylamino)-carbonyl)-3,4-tetrazolium-bis(4-methoxy-6-nitro) bezenesulfonic acid hydrate)] method as previously described (Jiang et al., 2004). Briefly, for MT-2 cells, 100 μl of a peptide at graded concentrations was added to an equal volume of cells ($1\times10^5$ cells/ml) in 96-well plates followed by incubation at 37° C. for 4 days, which ran parallel to the neutralization assay in MT-2 (except medium was added instead of virus). In the case of PBMC, $5\times10^5$ cells/ml were used and the cytotoxicity was measured after 7 days. After addition of XTT (PolySciences, Inc.), the soluble intracellular formazan was quantitated colorimetrically at 450 nm 4 hr later with a reference at 620 nm. The percent of cytotoxicity and the $CC_{50}$ values were calculated as above (Table 2 and Table 3).

Cytotoxicity assays were performed in parallel with the HIV-1 inhibition assays. The $CC_{50}$ (concentration of inhibitor required to produce 50% cytotoxicity) values of NYAD-201 and its analogs in MT-2 cells and PBMC are reported in Tables 2 and 3.

Figure 7:
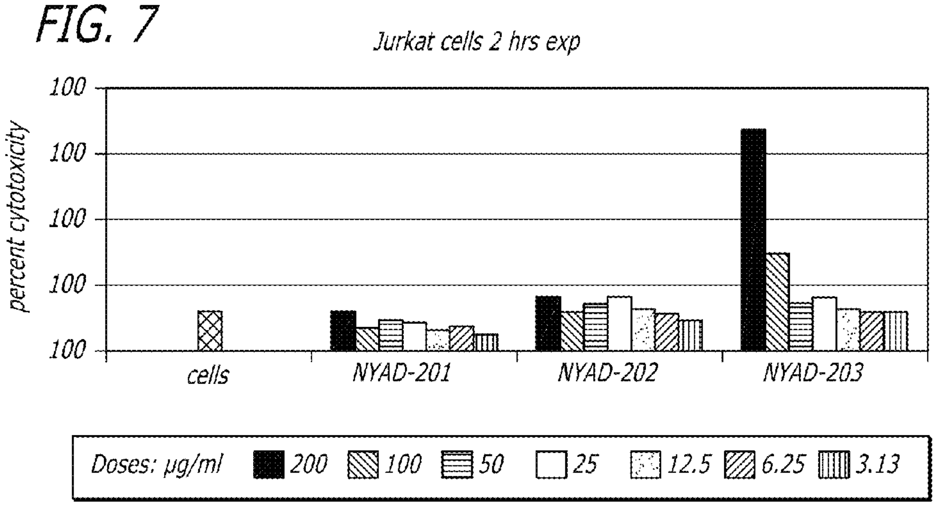
FIG. 7 depicts cytotoxicity of peptides NYAD-201, NYAD-202 and NYAD-203 in Jurkat cells after 2 hr of exposure.
Figure 8:
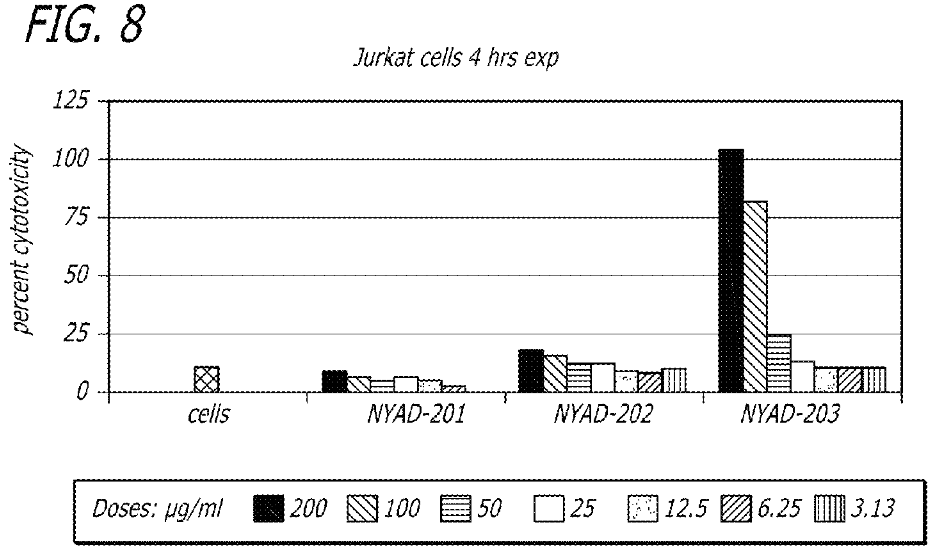
FIG. 8 depicts cytotoxicity of peptides NYAD-201, NYAD-202 and NYAD-203 in Jurkat cells after 4 hr of exposure.

Cytotoxicity was also evaluated in Jurkat cells using a Promega LDH leakage detection kit. Jurkat cells were plated at $10^4$ cells/well in a volume of 200 μl. The test was performed after 30 min, 2 hr and 4 hr of exposure to the NYAD-201, NYAD-202 and NYAD-203 compounds. NYAD-201 and NYAD-202 did not demonstrate toxicity even through they were not very soluble, NYAD-203 was more toxic at the two higher doses (FIGS. 6-8).

TABLE 1

Antiviral activity ($IC_{50}$) of stapled peptides against HIV-1 IIIB and their cytotoxicity ($CC_{50}$) in MT-2 cells

| Peptide | $IC_{50}$ (μM) ± SD | $CC_{50}$ (μM) ± SD |
|---|---|---|
| NYAD-201 | 4.29 ± 0.62 | >115 |
| NYAD-202 | 2.36 ± 0.33 | 30.2 ± 4.32 |
| NYAD-203 | 6.29 ± 0.54 | 13.24 ± 0.5 |
| NYAD-210 | 5.15 ± 0.76 | >112 |
| NYAD-212 | 5.95 ± 0.33 | >102 |
| NYAD-214 | 17.4 ± 0.90 | >48 |
| NYAD-215* | >56 | >112 |
| NYAD-218 | 4.6 ± 0.40 | 67.3 ± 4.4 |
| NYAD-219 | 3.7 ± 0.06 | >106 |
| NYAD-220 | >52.7 | >105.4 |
| NYAD-221 | 7.97 ± 1.03 | >140.4 |
| NYAD-222 | 9.3 ± 1.6 | >130 |
| NYAD-223 | 7.2 ± 1.2 | >124.4 |

*peptide with scrambled NYAD-201 sequence.

TABLE 2

Antiviral activity ($IC_{50}$) and cytotoxicity ($CC_{50}$) of NYAD-201, NYAD-202 and NYAD-203 in laboratory-adapted and primary HIV-1 isolates

| HIV-1 virus | Subtype | Cell Type | Coreceptor | $IC_{50}$ (μM ± SD) NYAD-201 | NYAD-202 | NYAD-203 |
|---|---|---|---|---|---|---|
| Laboratory Strains | | | | | | |
| IIIB | B | MT-2 | X4 | 4.29 ± 0.62 | 2.36 ± 0.33 | 6.29 ± 0.54 |
| MN | B | MT-2 | X4 | 3.03 ± 0.61 | 2.47 ± 0.71 | |
| SF2 | B | MT-2 | R5X4 | 5.06 ± 1.37 | 4.48 ± 0.84 | |
| RF | B | MT-2 | X4 | 2.84 ± 0.63 | 2.64 ± 0.39 | |
| BaL | B | PBMC | R5 | 4.73 ± 1.92 | 2.23 ± 0.44 | |
| 89.6 | B | PBMC | R5X4 | 5.21 ± 0.87 | 3.47 ± 0.22 | |
| RT-Resistant Isolate | | | | | | |
| AZT-R | B | MT-2 | X4 | 8.0 ± 1.27 | 4.53 ± 1.19 | 11.1 ± 3.82 |
| PR-Resistant Isolate | | | | | | |
| HIV-$1_{RF/L\text{-}323\text{-}12\text{-}3}$ | B | MT-2 | X4 | 5.6 ± 0.5 | 3.5 ± 0.6 | |
| Primary isolates | | | | | | |
| 93RW024 | A | PBMC | R5X4 | 9.88 ± 0.3 | 3.71 ± 0.19 | |
| 92UG029 | A | PBMC | X4 | 7.88 ± 1.01 | 3.97 ± 0.47 | |
| 92US657 | B | PBMC | R5 | 6.72 ± 0.98 | 3.61 ± 0.57 | |
| 93IN101 | C | PBMC | R5 | 1.58 ± 0.57 | 5.53 ± 0.39 | |
| 98CN009 | C | PBMC | R5 | 5.31 ± 0.83 | 4.08 ± 0.92 | |
| CMU02 | EA | PBMC | X4 | 7.36 ± 0.69 | 4.2 ± 0.01 | |
| 93BR020 | F | PBMC | R5X4 | 2.78 ± 0.57 | 2.51 ± 0.43 | |
| RU570 | G | PBMC | R5 | 7.48 ± 1.21 | 6.34 ± 2.22 | |
| BCF02 | (Group 0) | PBMC | R5 | 15.84 ± 3.43 | 6.2 ± 1.2 | |

| Peptides | $CC_{50}$ (μM) in MT-2 | $CC_{50}$ (μM)in PBMC |
|---|---|---|
| NYAD-201 | >115 | >115 |
| NYAD-202 | 30.2 ± 4.32 | >116 |
| NYAD-203 | 13.24 ± 0.5 | 15.96 ± 1.47 |

Example 6

Infectivity of the HIV-1 Virus Released from Infected MT-2 Cells after Treatment with NYAD-201 and NYAD-202

$5\times10^4$/ml MT-2 cells were infected with HIV-1 IIIB (MOI=0.01) in the presence of different concentrations of stapled peptides NYAD-201 and NYAD-202. Control cells were untreated and treated with 1 μg/ml of AMD3100 (CXCR-4 receptor inhibitor) or with 500 nM of nelfinavir (NFV) (HIV-1 protease inhibitor). Following overnight incubation, the medium was completely removed and replaced with fresh medium. On the fourth day post-infection, the supernatants were collected and filtered with a 0.45 μm PVDF membrane. One aliquot of the supernatants from each sample was mixed 1:1 with a solution of 5% Triton X-100 for p24 quantification, and stored at 4° C., another aliquot was immediately frozen at −80° C. and used to compare the infectivity of the viral particles released by NYAD-201 and NYAD-202 treated cells to the viral particles released by untreated cells. The protein p24 was first quantified by sandwich-ELISA, then the viral samples were normalized for the p24 content and titered to calculate the $TCID_{50}$. MT-2 cells were infected with a two fold dilutions of virus from NYAD-201 and NYAD-202 treated and untreated cells. Following on incubation ¾ of the medium containing the inoculum was replaced with fresh medium. On the fourth day post infection supernatants were collected for p24 quantification by sandwich-ELISA and the $TCID_{50}$ was calculated by the Spearman-Karber statistical method.

Neutralization experiments demonstrated a decrease in HIV-1 viral particle release by NYAD-201 and NYAD-202 treated MT-2 cells. The non-limiting hypothesis of the present inventors is that NYAD-201 and NYAD-202 interfere with viral uncoating, viral assembly and maturation inducing irreparable damage to the viral particles newly produced and released in the supernatant.

Figure 9:
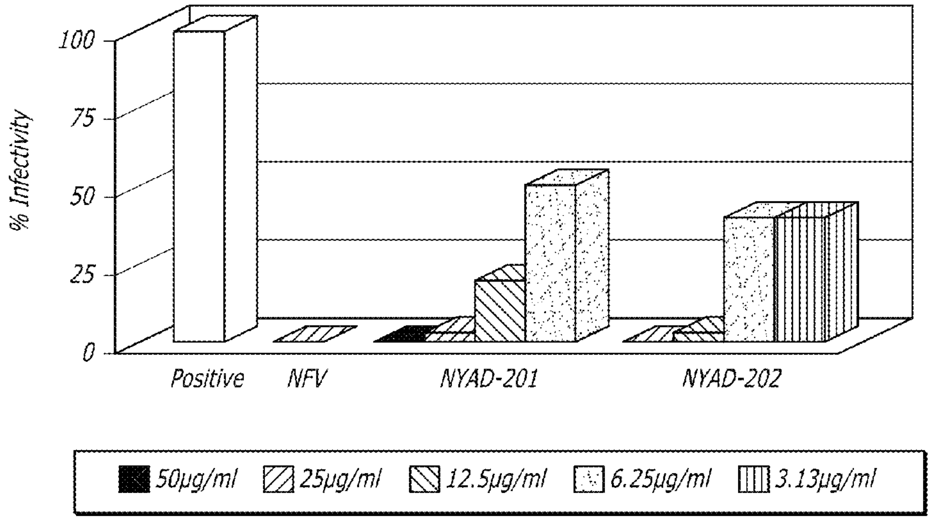
FIG. 9 depicts infectivity of HIV-1 virus released from MT-2 cells after treatment with NYAD-201 and NYAD-202.

For these reasons, not only the quantity but also the quality of the viral particles released in the supernatant was evaluated. First, the p24/viral particles released in the supernatant following NYAD-201 and NYAD-202 treatment were quantified, then starting with the same amount of p24 per sample, the viruses released in the supernatant were titered. The $TCID_{50}$ was calculated and expressed as percentage infectivity with respect to the untreated positive control. As expected, the virus produced by NFV-treated cells as well as the viruses produced by the cells treated with the two higher doses of the stapled peptides, NYAD-201 and NYAD-202, was not infectious or slightly infectious (FIG. 9). Additionally, only 50% and 40% of the virus produced by the cells treated with the lower doses of NYAD-201 (6.25 μg/ml) and NYAD-202 (6.25 and 3.13 μg/ml), respectively, was infectious. These data support the hypothesis that NYAD-201 and NYAD-202 may interfere with viral uncoating, assembly and/or viral maturation.

Figure 10:
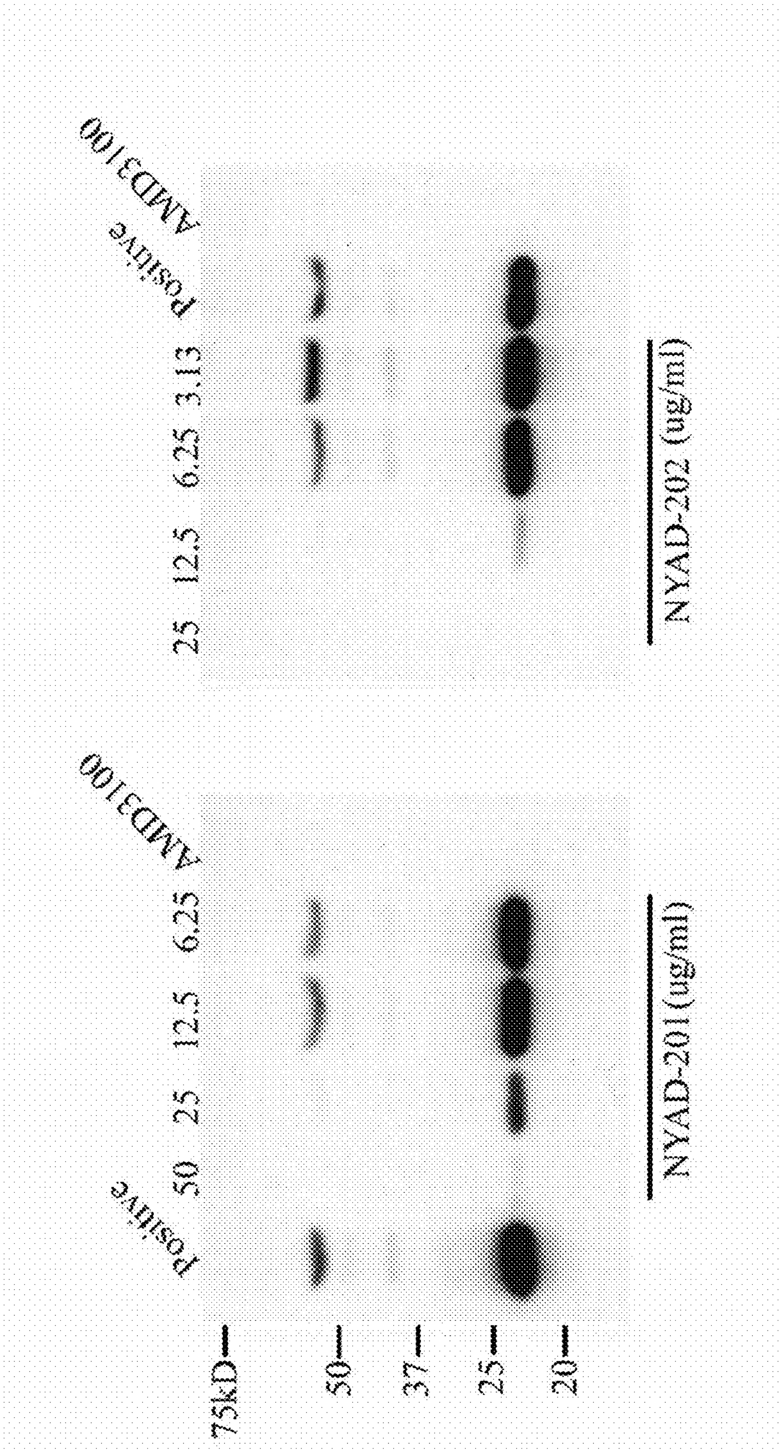
FIG. 10 depicts a Western blot analysis of HIV-1 virion-associated proteins in the supernatant of MT-2 cells treated with NYAD-201 and NYAD-202.

Western Blot $5\times10^4$/ml MT-2 cells were infected with HIV-1 IIIB (MOI=0.01) in the presence of different concentrations of stapled peptides, NYAD-201 and NYAD-202. Control cells were untreated and treated with 1 μg/ml of AMD3100. Following overnight incubation, the medium was completely removed and replaced with fresh medium. On the fourth day post-infection, the supernatants were filtered and ultra-centrifuged through a 20% sucrose cushion for 2 hr at 27,000 rpm with a SW28 rotor to concentrate the viral particles. Viral pellets were slowly re-suspended and processed for protein analysis. The same volume of viral proteins were resolved on a NuPAGE Novex 4-12% Bis-Tris Gel (Invitrogen). Proteins were then visualized by western blot and immuno-detected with HIV-1 anti-p24 Gag monoclonal antibody (NIH AIDS Research and Reference Reagent Program) (FIG. 10).

Same amounts of protein preparations from viral particles released in the supernatant by NYAD-201- and NYAD-202-treated and untreated cells were immunodetected with an anti-p24 mAb. FIG. 10 depicts that treatment with NYAD-201 and NYAD-202 induced a dose-dependent decrease in p24 and p55 levels confirming the data obtained with the neutralization experiments. These results suggest that NYAD-201 and NYAD-202 may also have effect on viral budding.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method for treatment of human immunodeficiency virus in a subject in need thereof, the method comprising:

administering to the subject a composition comprising an isolated peptide comprising a sequence from 14 to 21 amino acids in length, wherein two of the amino acids are unnatural amino acids having either R or S stereochemistry at the α-carbon;

wherein the α-carbon of the unnatural amino acids comprises a methyl group and an olefinic group, where the two olefinic groups of the unnatural amino acids are on the same side of the α-helix and are joined to form a cross-link between the two unnatural amino acids;

wherein the sequence of the peptide comprises (Q/A)(E/A/K)(V/W)(E/K)NW(M/A)TETLL(V/K)(QAE) (SEQ ID NO:18);

wherein the two unnatural amino acids replace two of the amino acids at any positions four amino acids apart (i and 1+4) or seven amino acids apart (i and i+7); and wherein the cross-link between the two unnatural amino acids is a C1-C10 alkyl, alkenyl, alkynyl, $(R1\text{-}K\text{-}R1)_n$, each of which is substituted with a 0-C6 R2, wherein R1 is an alkyl, alkenyl or alkynyl, K is O, S, SO, $SO_2$, CO, CONR4, or

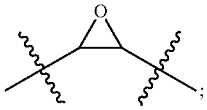 [SMILES: *C1OC1*]
;

R2 is a halo, C1-C10 alkyl, OR3, $N(R3)_2$, SR3 SOR3, $SO_2R3$, $CO_2R3$, R3, a fluorescent moiety or a radio-isotope;

R3 is H or a C1-C10 alkyl;

R4 is H, alkyl or a therapeutic agent; and n is an integer from 1-4.

2. The method of claim 1, wherein said unnatural amino acid is (S)-α-2-(4'-pentenyl)alanine or (R)-α-2-(7'-octenyl) alanine.

3. The method of claim 1, wherein the unnatural amino acids replace the sixth and tenth amino acids of the peptide.

4. The method of claim 1, wherein the cross-link between the two unnatural amino acids comprises:

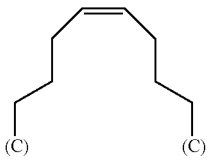

Or

-continued

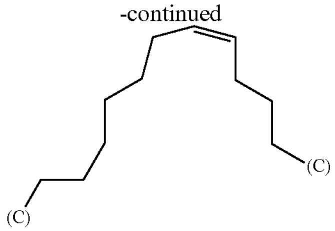

wherein the (C)s are the α-carbons of the unnatural amino acids.

5. The method of claim 1, wherein the sequence is SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:13, SEQ ID NO:14, SEQ ID NO:15, SEQ ID NO:16, or SEQ ID NO:17.

6. The method of claim 1, wherein R4 is H or alkyl.

7. The method of claim 1, wherein the composition further comprises a pharmaceutically acceptable carrier.

* * * * *